United States Patent [19]

Sugimoto et al.

[11] Patent Number: 5,688,671
[45] Date of Patent: Nov. 18, 1997

[54] MUTANT ASPARTOKINASE GENE

[75] Inventors: Masakazu Sugimoto; Yuri Ogawa; Tomoko Suzuki; Akiko Tanaka; Hiroshi Matsui, all of Kanagawa, Japan

[73] Assignee: Ajinomoto Co., Inc., Tokyo, Japan

[21] Appl. No.: 532,828

[22] PCT Filed: Dec. 14, 1993

[86] PCT No.: PCT/JP93/01809

§ 371 Date: Oct. 27, 1995

§ 102(e) Date: Oct. 27, 1995

[87] PCT Pub. No.: WO94/25605

PCT Pub. Date: Nov. 10, 1994

[30] Foreign Application Priority Data

Apr. 27, 1993 [JP] Japan ................................. 5-101450

[51] Int. Cl.⁶ ............................ C12P 13/08; C12N 9/12
[52] U.S. Cl. ...................... 435/115; 435/194; 435/252.32; 536/23.2
[58] Field of Search ........................... 435/69.1, 115, 435/172.1, 194, 252.32, 320.1, 840, 843; 536/23.2

[56] References Cited

FOREIGN PATENT DOCUMENTS 57-063095  4/1982  Japan .

OTHER PUBLICATIONS

Schrumpf et al (1992) Appl Microbiol Biotech 37:566–571 "Isolation and Prominent Characteristics of an L–lysine Hyperproducing Strain . . .".

Kalinowski et al (1991) Molec. Micro. 5:1197–1204.

Mitsubishi Petrochemical Co., Ltd., Sequence Database Entry Based on JO6261766-A (Published Sep. 20, 1994).

*Primary Examiner*—Robert A. Wax
*Assistant Examiner*—Daniel Mytelka
*Attorney, Agent, or Firm*—Oblon, Spivak, McClelland, Maier & Neustadt, P.C.

[57] ABSTRACT

Recombinant DNA replicable in microorganisms belonging to the genus Corynebacterium, which contains a DNA fragment coding for an aspartokinase α-subunit protein originating from a bacterium belonging to the genus Corynebacterium, in which synergistic feedback inhibition by L-lysine and L-threonine is substantially desensitized, and a DNA fragment coding for an aspartokinase β-subunit protein originating from a bacterium belonging to the genus Corynebacterium, in which synergistic feedback inhibition by L-lysine and L-threonine is substantially desensitized, is introduced into a microorganism belonging to the genus Corynebacterium. Thus a transformant having enhanced production and excretion speeds of L-lysine is obtained. The transformant is cultivated in an appropriate medium, and produced L-lysine is separated.

12 Claims, 6 Drawing Sheets

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
( A ) LENGTH: 1643 nucleotides
( B ) TYPE: nucleic acid ( C ) STRANDEDNESS: double
( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
( A ) ORGANISM: Corynebacterium glutamicum
( B ) STRAIN: ATCC 13869

( x i ) SEQUENCE DESCRIPTION: SEQ ID NO:1:

| | | | | | | |
|---|---|---|---|---|---|---|
| TCGCGAAGTA | GCACCTGTCA | CTTTTGTCTC | AAATATTAAA | TCGAATATCA | ATATACGGTC | 60 |
| TGTTTATTGG | AACGCATCCC | AGTGGCTGAG | ACGCATCCGC | TAAAGCCCCA | GGAACCCTGT | 120 |
| GCAGAAAGAA | AACACTCCTC | TGGCTAGGTA | GACACAGTTT | ATAAAGGTAG | AGTTGAGCGG | 180 |
| GTAACTGTCA | GCACGTAGAT | CGAAAGGTGC | ACAAGGTGG | CCCTGGTCGT | ACAGAAATAT | 240 |
| GGCGGTTCCT | CGCTTGAGAG | TGCGGAACGC | ATTAGAAACG | TCGCTGAACG | GATCGTTGCC | 300 |
| ACCAAGAAGG | CTGGAAATGA | TGTCGTGGTT | GTCTGCTCCG | CAATGGGAGA | CACCACGGAT | 360 |
| GAACTTCTAG | AACTTGCAGC | GGCAGTGAAT | CCCGTTCCGC | CAGCTCGTGA | AATGGATATG | 420 |
| CTCCTGACTG | CTGGTGAGCG | TATTTCTAAC | GCTCTCGTCG | CCATGGCTAT | TGAGTCCCTT | 480 |
| GGCGCAGAAG | CTCAATCTTT | CACTGGCTCT | CAGGCTGGTG | TGCTCACCAC | CGAGCGCCAC | 540 |
| GGAAACGCAC | GCATTGTTGA | CGTCACACCG | GGTCGTGTGC | GTGAAGCACT | CGATGAGGGC | 600 |
| AAGATCTGCA | TTGTTGCTGG | TTTTCAGGGT | GTTAATAAAG | AAACCCGCGA | TGTCACCACG | 660 |
| TTGGGTCGTG | GTGGTTCTGA | CACCACTGCA | GTTGCGTTGG | CAGCTGCTTT | GAACGCTGAT | 720 |
| GTGTGTGAGA | TTTACTCGGA | CGTTGACGGT | GTGTATACCG | CTGACCCGCG | CATCGTTCCT | 780 |
| AATGCACAGA | AGCTGGAAAA | GCTCAGCTTC | GAAGAAATGC | TGGAACTTGC | TGCTGTTGGC | 840 |
| TCCAAGATTT | TGGTGCTGCG | CAGTGTTGAA | TACGCTCGTG | CATTCAATGT | GCCACTTCGC | 900 |
| GTACGCTCGT | CTTATAGTAA | TGATCCCGGC | ACTTTGATTG | CCGGCTCTAT | GGAGGATATT | 960 |
| CCTGTGGAAG | AAGCAGTCCT | TACCGGTGTC | GCAACCGACA | AGTCCGAAGC | CAAAGTAACC | 1020 |
| GTTCTGGGTA | TTTCCGATAA | GCCAGGCGAG | GCTGCCAAGG | TTTTCCGTGC | GTTGGCTGAT | 1080 |
| GCAGAAATCA | ACATTGACAT | GGTTCTGCAG | AACGTCTCCT | CTGTGGAAGA | CGGCACCACC | 1140 |
| GACATCACGT | TCACCTGCCC | TCGCGCTGAC | GGACGCCGTG | CGATGGAGAT | CTTGAAGAAG | 1200 |
| CTTCAGGTTC | AGGGCAACTG | GACCAATGTG | CTTTACGACG | ACCAGGTCGG | CAAAGTCTCC | 1260 |
| CTCGTGGGTG | CTGGCATGAA | GTCTCACCCA | GGTGTTACCG | CAGAGTTCAT | GGAAGCTCTG | 1320 |
| CGCGATGTCA | ACGTGAACAT | CGAATTGATT | TCCACCTCTG | AGATCCGCAT | TTCCGTGCTG | 1380 |
| ATCCGTGAAG | ATGATCTGGA | TGCTGCTGCA | CGTGCATTGC | ATGAGCAGTT | CCAGCTGGGC | 1440 |
| GGCGAAGACG | AAGCCGTCGT | TTATGCAGGC | ACCGGACGCT | AAAGTTTTAA | AGGAGTAGTT | 1500 |
| TTACAATGAC | CACCATCGCA | GTTGTTGGTG | CAACCGGCCA | GGTCGGCCAG | GTTATGCGCA | 1560 |
| CCCTTTTGGA | AGAGCGCAAT | TTCCCAGCTG | ACACTGTTCG | TTTCTTTGCT | TCCCCGCGTT | 1620 |
| CCGCAGGCCG | TAAGATTGAA | TTC | | | | 1643 |

( 2 ) INFORMATION FOR SEQ ID NO:2:

( i ) SEQUENCE CHARACTERISTICS:
( A ) LENGTH: 1643 nucleotides
( B ) TYPE: nucleic acid
( C ) STRANDEDNESS: double
( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
    ( A ) ORGANISM: Corynebacterium glutamicum
    ( B ) STRAIN: AJ3463

( x i ) SEQUENCE DESCRIPTION: SEQ ID NO:2:

| | | | | | | |
|---|---|---|---|---|---|---|
| TCGCGAAGTA | GCACCTGTCA | CTTTTGTCTC | AAATATTAAA | TCGAATATCA | ATATACGGTC | 60 |
| TGTTTATTGG | AACGCATCCC | AGTGGCTGAG | ACGCATCCGC | TAAAGCCCCA | GGAACCCTGT | 120 |
| GCAGAAAGAA | AACACTCCTC | TGGCTAGGTA | GACACAGTTT | ATAAAGGTAG | AGTTGAGCGG | 180 |
| GTAACTGTCA | GCACGTAGAT | CGAAAGGTGC | ACAAAGGTGG | CCCTGGTCGT | ACAGAAATAT | 240 |
| GGCGGTTCCT | CGCTTGAGAG | TGCGGAACGC | ATTAGAAACG | TCGCTGAACG | GATCGTTGCC | 300 |
| ACCAAGAAGG | CTGGAAATGA | TGTCGTGGTT | GTCTGCTCCG | CAATGGAGA | CACCACGGAT | 360 |
| GAACTTCTAG | AACTTGCAGC | GGCAGTGAAT | CCCGTTCCGC | CAGCTCGTGA | AATGGATATG | 420 |
| CTCCTGACTG | CTGGTGAGCG | TATTTCTAAC | GCTCTCGTCG | CCATGGCTAT | TGAGTCCCTT | 480 |
| GGCGCAGAAG | CTCAATCTTT | CACTGGCTCT | CAGGCTGGTG | TGCTCACCAC | CGAGCGCCAC | 540 |
| GGAAACGCAC | GCATTGTTGA | CGTCACACCG | GGTCGTGTGC | GTGAAGCACT | CGATGAGGGC | 600 |
| AAGATCTGCA | TTGTTGCTGG | TTTTCAGGGT | GTTAATAAAG | AAACCCGCGA | TGTCACCACG | 660 |
| TTGGGTCGTG | GTGGTTCTGA | CACCACTGCA | GTTGCGTTGG | CAGCTGCTTT | GAACGCTGAT | 720 |
| GTGTGTGAGA | TTTACTCGGA | CGTTGACGGT | GTGTATACCG | CTGACCCGCG | CATCGTTCCT | 780 |
| AATGCACAGA | AGCTGGAAAA | GCTCAGCTTC | GAAGAAATGC | TGGAACTTGC | TGCTGTTGGC | 840 |
| TCCAAGATTT | TGGTGCTGCG | CAGTGTTGAA | TACGCTCGTG | CATTCAATGT | GCCACTTCGC | 900 |
| GTACGCTCGT | CTTATAGTAA | TGATCCCGGC | ACTTTGATTG | CCGGCTCTAT | GGAGGATATT | 960 |
| CCTGTGGAAG | AAGCAGTCCT | TACCGGTGTC | GCAACCGACA | AGTCCGAAGC | CAAAGTAACC | 1020 |
| GTTCTGGGTA | TTTCCGATAA | GCCAGGCGAG | ACTGCCAAGG | TTTTCCGTGC | GTTGGCTGAT | 1080 |
| GCAGAAATCA | ACATTGACAT | GGTTCTGCAG | AACGTCTCCT | CTGTGGAAGA | CGGCACCACC | 1140 |
| GACATCACGT | TCACCTGCCC | TCGCGCTGAC | GGACGCCGTG | CGATGGAGAT | CTTGAAGAAG | 1200 |
| CTTCAGGTTC | AGGGCAACTG | GACCAATGTG | CTTTACGACG | ACCAGGTCGG | CAAAGTCTCC | 1260 |
| CTCGTGGGTG | CTGGCATGAA | GTCTCACCCA | GGTGTTACCG | CAGAGTTCAT | GGAAGCTCTG | 1320 |
| CGCGATGTCA | ACGTGAACAT | CGAATTGATT | TCCACCTCTG | AGATCCGCAT | TTCCGTGCTG | 1380 |
| ATCCGTGAAG | ATGATCTGGA | TGCTGCTGCA | CGTGCATTGC | ATGAGCAGTT | CCAGCTGGGC | 1440 |
| GGCGAAGACG | AAGCCGTCGT | TTATGCAGGC | ACCGGACGCT | AAAGTTTTAA | AGGAGTAGTT | 1500 |
| TTACAATGAC | CACCATCGCA | GTTGTTGGTG | CAACCGGCCA | GGTCGGCCAG | GTTATGCGCA | 1560 |
| CCCTTTTGGA | AGAGCGCAAT | TTCCCAGCTG | ACACTGTTCG | TTTCTTTGCT | TCCCCGCGTT | 1620 |
| CCGCAGGCCG | TAAGATTGAA | TTC | | | | 1643 |

( 2 ) INFORMATION FOR SEQ ID NO:3:

( i ) SEQUENCE CHARACTERISTICS:
        ( A ) LENGTH: 421 amino acids
        ( B ) TYPE: amino acid
        ( D ) TOPOLOGY: linear ( i i ) MOLECULE TYPE: peptide ( i i i ) HYPOTHETICAL: NO -continued ( i v ) ANTI-SENSE: NO ( v i ) ORIGINAL SOURCE:
    ( A ) ORGANISM: Corynebacterium glutamicum
    ( B ) STRAIN: ATCC13869

( x i ) SEQUENCE DESCRIPTION: SEQ ID NO:3:

```
Met Ala Leu Val Val Gln Lys Tyr Gly Gly Ser Ser Leu Glu Ser Ala
 1               5                  10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
            35                  40                  45

Glu Leu Leu Glu Leu Ala Ala Ala Val Asn Pro Val Pro Pro Ala Arg
 50                  55                  60

Glu Met Asp Met Leu Leu Thr Ala Gly Glu Arg Ile Ser Asn Ala Leu
 65                  70                  75                  80

Val Ala Met Ala Ile Glu Ser Leu Gly Ala Glu Ala Gln Ser Phe Thr
                 85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
            115                 120                 125

Lys Ile Cys Ile Val Ala Gly Phe Gln Gly Val Asn Lys Glu Thr Arg
130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
            195                 200                 205

Ser Lys Ile Leu Val Leu Arg Ser Val Glu Tyr Ala Arg Ala Phe Asn
210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
            275                 280                 285

Ala Glu Ile Asn Ile Asp Met Val Leu Gln Asn Val Ser Ser Val Glu
290                 295                 300

Asp Gly Thr Thr Asp Ile Thr Phe Thr Cys Pro Arg Ala Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
            355                 360                 365

Arg Asp Val Asn Val Asn Ile Glu Leu Ile Ser Thr Ser Glu Ile Arg
370                 375                 380
```

| Ile | Ser | Val | Leu | Ile | Arg | Glu | Asp | Leu | Asp | Ala | Ala | Ala | Arg | Ala |
|-----|-----|-----|-----|-----|-----|-----|-----|-----|-----|-----|-----|-----|-----|-----|
| 385 |     |     |     |     | 390 |     |     |     | 395 |     |     |     |     | 400 |

| Leu | His | Glu | Gln | Phe | Gln | Leu | Gly | Gly | Glu | Asp | Glu | Ala | Val | Val | Tyr |
|-----|-----|-----|-----|-----|-----|-----|-----|-----|-----|-----|-----|-----|-----|-----|-----|
|     |     |     |     | 405 |     |     |     |     | 410 |     |     |     |     | 415 |     |

| Ala | Gly | Thr | Gly | Arg |
|-----|-----|-----|-----|-----|
|     |     |     |     | 420 |

( 2 ) INFORMATION FOR SEQ ID NO:4:

( i ) SEQUENCE CHARACTERISTICS:
        ( A ) LENGTH: 421 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Corynebacterium glutamicum
        ( B ) STRAIN: AJ3463

( x i ) SEQUENCE DESCRIPTION: SEQ ID NO:4:

| Met | Ala | Leu | Val | Val | Gln | Lys | Tyr | Gly | Gly | Ser | Ser | Leu | Glu | Ser | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Arg | Ile | Arg | Asn | Val | Ala | Glu | Arg | Ile | Val | Ala | Thr | Lys | Lys | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Asn | Asp | Val | Val | Val | Val | Cys | Ser | Ala | Met | Gly | Asp | Thr | Thr | Asp |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Glu | Leu | Leu | Glu | Leu | Ala | Ala | Ala | Val | Asn | Pro | Val | Pro | Pro | Ala | Arg |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Glu | Met | Asp | Met | Leu | Leu | Thr | Ala | Gly | Glu | Arg | Ile | Ser | Asn | Ala | Leu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Val | Ala | Met | Ala | Ile | Glu | Ser | Leu | Gly | Ala | Glu | Ala | Gln | Ser | Phe | Thr |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Gly | Ser | Gln | Ala | Gly | Val | Leu | Thr | Thr | Glu | Arg | His | Gly | Asn | Ala | Arg |
|-----|-----|-----|-----|-----|-----|-----|-----|-----|-----|-----|-----|-----|-----|-----|-----|
|     |     |     |     | 100 |     |     |     |     | 105 |     |     |     |     | 110 |     |

| Ile | Val | Asp | Val | Thr | Pro | Gly | Arg | Val | Arg | Glu | Ala | Leu | Asp | Glu | Gly |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Lys | Ile | Cys | Ile | Val | Ala | Gly | Phe | Gln | Gly | Val | Asn | Lys | Glu | Thr | Arg |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Asp | Val | Thr | Thr | Leu | Gly | Arg | Gly | Gly | Ser | Asp | Thr | Thr | Ala | Val | Ala |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Leu | Ala | Ala | Ala | Leu | Asn | Ala | Asp | Val | Cys | Glu | Ile | Tyr | Ser | Asp | Val |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Asp | Gly | Val | Tyr | Thr | Ala | Asp | Pro | Arg | Ile | Val | Pro | Asn | Ala | Gln | Lys |
|-----|-----|-----|-----|-----|-----|-----|-----|-----|-----|-----|-----|-----|-----|-----|-----|
|     |     |     |     | 180 |     |     |     |     | 185 |     |     |     |     | 190 |     |

| Leu | Glu | Lys | Leu | Ser | Phe | Glu | Glu | Met | Leu | Glu | Leu | Ala | Ala | Val | Gly |
|-----|-----|-----|-----|-----|-----|-----|-----|-----|-----|-----|-----|-----|-----|-----|-----|
|     |     |     | 195 |     |     |     |     | 200 |     |     |     |     | 205 |     |     |

| Ser | Lys | Ile | Leu | Val | Leu | Arg | Ser | Val | Glu | Tyr | Ala | Arg | Ala | Phe | Asn |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Val | Pro | Leu | Arg | Val | Arg | Ser | Ser | Tyr | Ser | Asn | Asp | Pro | Gly | Thr | Leu |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Ile | Ala | Gly | Ser | Met | Glu | Asp | Ile | Pro | Val | Glu | Glu | Ala | Val | Leu | Thr |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Gly | Val | Ala | Thr | Asp | Lys | Ser | Glu | Ala | Lys | Val | Thr | Val | Leu | Gly | Ile |
|-----|-----|-----|-----|-----|-----|-----|-----|-----|-----|-----|-----|-----|-----|-----|-----|
|     |     |     |     | 260 |     |     |     |     | 265 |     |     |     |     | 270 |     |

-continued

```
Ser  Asp  Lys  Pro  Gly  Glu  Thr  Ala  Lys  Val  Phe  Arg  Ala  Leu  Ala  Asp
          275                     280                      285

Ala  Glu  Ile  Asn  Ile  Asp  Met  Val  Leu  Gln  Asn  Val  Ser  Ser  Val  Glu
          290                     295                      300

Asp  Gly  Thr  Thr  Asp  Ile  Thr  Phe  Thr  Cys  Pro  Arg  Ala  Asp  Gly  Arg
305                      310                    315                          320

Arg  Ala  Met  Glu  Ile  Leu  Lys  Lys  Leu  Gln  Val  Gln  Gly  Asn  Trp  Thr
                    325                      330                     335

Asn  Val  Leu  Tyr  Asp  Asp  Gln  Val  Gly  Lys  Val  Ser  Leu  Val  Gly  Ala
               340                      345                     350

Gly  Met  Lys  Ser  His  Pro  Gly  Val  Thr  Ala  Glu  Phe  Met  Glu  Ala  Leu
          355                     360                      365

Arg  Asp  Val  Asn  Val  Asn  Ile  Glu  Leu  Ile  Ser  Thr  Ser  Glu  Ile  Arg
     370                     375                    380

Ile  Ser  Val  Leu  Ile  Arg  Glu  Asp  Asp  Leu  Asp  Ala  Ala  Ala  Arg  Ala
385                      390                    395                          400

Leu  His  Glu  Gln  Phe  Gln  Leu  Gly  Gly  Glu  Asp  Glu  Ala  Val  Val  Tyr
                    405                      410                     415

Ala  Gly  Thr  Gly  Arg
                    420
```

( 2 ) INFORMATION FOR SEQ ID NO:5:

( i ) SEQUENCE CHARACTERISTICS:
( A ) LENGTH: 172 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
( A ) ORGANISM: Corynebacterium glutamicum
( B ) STRAIN: ATCC13869

( x i ) SEQUENCE DESCRIPTION: SEQ ID NO:5:

```
Met  Glu  Glu  Ala  Val  Leu  Thr  Gly  Val  Ala  Thr  Asp  Lys  Ser  Glu  Ala
1                   5                        10                     15

Lys  Val  Thr  Val  Leu  Gly  Ile  Ser  Asp  Lys  Pro  Gly  Glu  Ala  Ala  Lys
               20                       25                      30

Val  Phe  Arg  Ala  Leu  Ala  Asp  Ala  Glu  Ile  Asn  Ile  Asp  Met  Val  Leu
          35                      40                       45

Gln  Asn  Val  Ser  Ser  Val  Glu  Asp  Gly  Thr  Thr  Asp  Ile  Thr  Phe  Thr
     50                      55                      60

Cys  Pro  Arg  Ala  Asp  Gly  Arg  Arg  Ala  Met  Glu  Ile  Leu  Lys  Lys  Leu
65                       70                     75                           80

Gln  Val  Gln  Gly  Asn  Trp  Thr  Asn  Val  Leu  Tyr  Asp  Asp  Gln  Val  Gly
                    85                       90                      95

Lys  Val  Ser  Leu  Val  Gly  Ala  Gly  Met  Lys  Ser  His  Pro  Gly  Val  Thr
               100                      105                     110

Ala  Glu  Phe  Met  Glu  Ala  Leu  Arg  Asp  Val  Asn  Val  Asn  Ile  Glu  Leu
          115                     120                      125

Ile  Ser  Thr  Ser  Glu  Ile  Arg  Ile  Ser  Val  Leu  Ile  Arg  Glu  Asp  Asp
     130                     135                     140

Leu  Asp  Ala  Ala  Ala  Arg  Ala  Leu  His  Glu  Gln  Phe  Gln  Leu  Gly  Gly
145                      150                    155                          160
```

```
Glu Asp Glu Ala Val Val Tyr Ala Gly Thr Gly Arg
            165                 170
```

( 2 ) INFORMATION FOR SEQ ID NO:6:

( i ) SEQUENCE CHARACTERISTICS:
        ( A ) LENGTH: 172 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Corynebacterium glutamicum
        ( B ) STRAIN: AJ3463

( x i ) SEQUENCE DESCRIPTION: SEQ ID NO:6:

```
Met Glu Glu Ala Val Leu Thr Gly Val Ala Thr Asp Lys Ser Glu Ala
 1               5                  10                  15
Lys Val Thr Val Leu Gly Ile Ser Asp Lys Pro Gly Glu Thr Ala Lys
                20                  25                  30
Val Phe Arg Ala Leu Ala Asp Ala Glu Ile Asn Ile Asp Met Val Leu
            35                  40                  45
Gln Asn Val Ser Ser Val Glu Asp Gly Thr Thr Asp Ile Thr Phe Thr
        50                  55                  60
Cys Pro Arg Ala Asp Gly Arg Arg Ala Met Glu Ile Leu Lys Lys Leu
 65                 70                  75                  80
Gln Val Gln Gly Asn Trp Thr Asn Val Leu Tyr Asp Asp Gln Val Gly
                85                  90                  95
Lys Val Ser Leu Val Gly Ala Gly Met Lys Ser His Pro Gly Val Thr
               100                 105                 110
Ala Glu Phe Met Glu Ala Leu Arg Asp Val Asn Val Asn Ile Glu Leu
           115                 120                 125
Ile Ser Thr Ser Glu Ile Arg Ile Ser Val Leu Ile Arg Glu Asp Asp
       130                 135                 140
Leu Asp Ala Ala Ala Arg Ala Leu His Glu Gln Phe Gln Leu Gly Gly
145                 150                 155                 160
Glu Asp Glu Ala Val Val Tyr Ala Gly Thr Gly Arg
                165                 170
```

( 2 ) INFORMATION FOR SEQ ID NO:7:

( i ) SEQUENCE CHARACTERISTICS:
        ( A ) LENGTH: 1643 nucleotides
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
        ( A ) ORGANISM: Corynebacterium glutamicum
        ( B ) STRAIN: ATCC13869

( i x ) FEATURE:
        ( A ) NAME/KEY: mat peptide
        ( B ) LOCATION: 217..1482

( x i ) SEQUENCE DESCRIPTION: SEQ ID NO:7:

```
TCGCGAAGTA GCACCTGTCA CTTTTGTCTC AAATATTAAA TCGAATATCA ATATACGGTC      60

TGTTTATTGG AACGCATCCC AGTGGCTGAG ACGCATCCGC TAAAGCCCCA GGAACCCTGT     120

GCAGAAAGAA AACACTCCTC TGGCTAGGTA GACACAGTTT ATAAAGGTAG AGTTGAGCGG     180

GTAACTGTCA GCACGTAGAT CGAAAGGTGC ACAAAG GTG GCC CTG GTC GTA CAG      234
                                         Met Ala Leu Val Val Gln
                                          1                5

AAA TAT GGC GGT TCC TCG CTT GAG AGT GCG GAA CGC ATT AGA AAC GTC      282
Lys Tyr Gly Gly Ser Ser Leu Glu Ser Ala Glu Arg Ile Arg Asn Val
            10              15                  20

GCT GAA CGG ATC GTT GCC ACC AAG AAG GCT GGA AAT GAT GTC GTG GTT      330
Ala Glu Arg Ile Val Ala Thr Lys Lys Ala Gly Asn Asp Val Val Val
        25              30                  35

GTC TGC TCC GCA ATG GGA GAC ACC ACG GAT GAA CTT CTA GAA CTT GCA      378
Val Cys Ser Ala Met Gly Asp Thr Thr Asp Glu Leu Leu Glu Leu Ala
    40              45                  50

GCG GCA GTG AAT CCC GTT CCG CCA GCT CGT GAA ATG GAT ATG CTC CTG      426
Ala Ala Val Asn Pro Val Pro Pro Ala Arg Glu Met Asp Met Leu Leu
55              60                  65                      70

ACT GCT GGT GAG CGT ATT TCT AAC GCT CTC GTC GCC ATG GCT ATT GAG      474
Thr Ala Gly Glu Arg Ile Ser Asn Ala Leu Val Ala Met Ala Ile Glu
            75                  80                  85

TCC CTT GGC GCA GAA GCT CAA TCT TTC ACT GGC TCT CAG GCT GGT GTG      522
Ser Leu Gly Ala Glu Ala Gln Ser Phe Thr Gly Ser Gln Ala Gly Val
        90                  95                 100

CTC ACC ACC GAG CGC CAC GGA AAC GCA CGC ATT GTT GAC GTC ACA CCG      570
Leu Thr Thr Glu Arg His Gly Asn Ala Arg Ile Val Asp Val Thr Pro
        105                 110                 115

GGT CGT GTG CGT GAA GCA CTC GAT GAG GGC AAG ATC TGC ATT GTT GCT      618
Gly Arg Val Arg Glu Ala Leu Asp Glu Gly Lys Ile Cys Ile Val Ala
120                 125                 130

GGT TTT CAG GGT GTT AAT AAA GAA ACC CGC GAT GTC ACC ACG TTG GGT      666
Gly Phe Gln Gly Val Asn Lys Glu Thr Arg Asp Val Thr Thr Leu Gly
135                 140                 145                 150

CGT GGT GGT TCT GAC ACC ACT GCA GTT GCG TTG GCA GCT GCT TTG AAC      714
Arg Gly Gly Ser Asp Thr Thr Ala Val Ala Leu Ala Ala Ala Leu Asn
                155                 160                 165

GCT GAT GTG TGT GAG ATT TAC TCG GAC GTT GAC GGT GTG TAT ACC GCT      762
Ala Asp Val Cys Glu Ile Tyr Ser Asp Val Asp Gly Val Tyr Thr Ala
            170                 175                 180

GAC CCG CGC ATC GTT CCT AAT GCA CAG AAG CTG GAA AAG CTC AGC TTC      810
Asp Pro Arg Ile Val Pro Asn Ala Gln Lys Leu Glu Lys Leu Ser Phe
        185                 190                 195

GAA GAA ATG CTG GAA CTT GCT GCT GTT GGC TCC AAG ATT TTG GTG CTG      858
Glu Glu Met Leu Glu Leu Ala Ala Val Gly Ser Lys Ile Leu Val Leu
        200                 205                 210

CGC AGT GTT GAA TAC GCT CGT GCA TTC AAT GTG CCA CTT CGC GTA CGC      906
Arg Ser Val Glu Tyr Ala Arg Ala Phe Asn Val Pro Leu Arg Val Arg
215                 220                 225                 230

TCG TCT TAT AGT AAT GAT CCC GGC ACT TTG ATT GCC GGC TCT ATG GAG      954
Ser Ser Tyr Ser Asn Asp Pro Gly Thr Leu Ile Ala Gly Ser Met Glu
                235                 240                 245

GAT ATT CCT GTG GAA GAA GCA GTC CTT ACC GGT GTC GCA ACC GAC AAG     1002
Asp Ile Pro Val Glu Glu Ala Val Leu Thr Gly Val Ala Thr Asp Lys
            250                 255                 260

TCC GAA GCC AAA GTA ACC GTT CTG GGT ATT TCC GAT AAG CCA GGC GAG     1050
Ser Glu Ala Lys Val Thr Val Leu Gly Ile Ser Asp Lys Pro Gly Glu
        265                 270                 275

GCT GCC AAG GTT TTC CGT GCG TTG GCT GAT GCA GAA ATC AAC ATT GAC     1098
```

-continued

| Ala | Ala | Lys | Val | Phe | Arg | Ala | Leu | Ala | Asp | Ala | Glu | Ile | Asn | Ile | Asp |
|     | 280 |     |     |     |     |     | 285 |     |     |     | 290 |     |     |     |     |

ATG GTT CTG CAG AAC GTC TCC TCT GTG GAA GAC GGC ACC ACC GAC ATC   1146
Met Val Leu Gln Asn Val Ser Ser Val Glu Asp Gly Thr Thr Asp Ile
295             300             305             310

ACG TTC ACC TGC CCT CGC GCT GAC GGA CGC CGT GCG ATG GAG ATC TTG   1194
Thr Phe Thr Cys Pro Arg Ala Asp Gly Arg Arg Ala Met Glu Ile Leu
            315             320             325

AAG AAG CTT CAG GTT CAG GGC AAC TGG ACC AAT GTG CTT TAC GAC GAC   1242
Lys Lys Leu Gln Val Gln Gly Asn Trp Thr Asn Val Leu Tyr Asp Asp
            330             335             340

CAG GTC GGC AAA GTC TCC CTC GTG GGT GCT GGC ATG AAG TCT CAC CCA   1290
Gln Val Gly Lys Val Ser Leu Val Gly Ala Gly Met Lys Ser His Pro
        345             350             355

GGT GTT ACC GCA GAG TTC ATG GAA GCT CTG CGC GAT GTC AAC GTG AAC   1338
Gly Val Thr Ala Glu Phe Met Glu Ala Leu Arg Asp Val Asn Val Asn
    360             365             370

ATC GAA TTG ATT TCC ACC TCT GAG ATC CGC ATT TCC GTG CTG ATC CGT   1386
Ile Glu Leu Ile Ser Thr Ser Glu Ile Arg Ile Ser Val Leu Ile Arg
375             380             385             390

GAA GAT GAT CTG GAT GCT GCT GCA CGT GCA TTG CAT GAG CAG TTC CAG   1434
Glu Asp Asp Leu Asp Ala Ala Ala Arg Ala Leu His Glu Gln Phe Gln
            395             400             405

CTG GGC GGC GAA GAC GAA GCC GTC GTT TAT GCA GGC ACC GGA CGC TAA   1482
Leu Gly Gly Glu Asp Glu Ala Val Val Tyr Ala Gly Thr Gly Arg
            410             415             420 421

AGTTTTAAAG GAGTAGTTTT ACAATGACCA CCATCGCAGT TGTTGGTGCA ACCGGCCAGG   1542

TCGGCCAGGT TATGCGCACC CTTTTGGAAG AGCGCAATTT CCCAGCTGAC ACTGTTCGTT   1602

TCTTTGCTTC CCCGCGTTCC GCAGGCCGTA AGATTGAATT C                      1643

( 2 ) INFORMATION FOR SEQ ID NO:8:

( i ) SEQUENCE CHARACTERISTICS:
        ( A ) LENGTH: 1643 nucleotides
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
        ( A ) ORGANISM: Corynebacterium glutamicum
        ( B ) STRAIN: AJ3463

( i x ) FEATURE:
        ( A ) NAME/KEY: mat peptide
        ( B ) LOCATION: 217..1482

( x i ) SEQUENCE DESCRIPTION: SEQ ID NO:8:

TCGCGAAGTA GCACCTGTCA CTTTTGTCTC AAATATTAAA TCGAATATCA ATATACGGTC   60

TGTTTATTGG AACGCATCCC AGTGGCTGAG ACGCATCCGC TAAAGCCCCA GGAACCCTGT   120

GCAGAAAGAA AACACTCCTC TGGCTAGGTA GACACAGTTT ATAAAGGTAG AGTTGAGCGG   180

GTAACTGTCA GCACGTAGAT CGAAAGGTGC ACAAAG GTG GCC CTG GTC GTA CAG   234
                                         Met Ala Leu Val Val Gln
                                          1               5

AAA TAT GGC GGT TCC TCG CTT GAG AGT GCG GAA CGC ATT AGA AAC GTC   282
Lys Tyr Gly Gly Ser Ser Leu Glu Ser Ala Glu Arg Ile Arg Asn Val
        10              15              20

-continued

| | | | | | | | | | | | | | | | | |
|---|---|---|---|---|---|---|---|---|---|---|---|---|---|---|---|---|
| GCT | GAA | CGG | ATC | GTT | GCC | ACC | AAG | AAG | GCT | GGA | AAT | GAT | GTC | GTG | GTT | 330 |
| Ala | Glu | Arg 25 | Ile | Val | Ala | Thr | Lys 30 | Lys | Ala | Gly | Asn | Asp 35 | Val | Val | Val | |
| GTC | TGC | TCC | GCA | ATG | GGA | GAC | ACC | ACG | GAT | GAA | CTT | CTA | GAA | CTT | GCA | 378 |
| Val | Cys 40 | Ser | Ala | Met | Gly | Asp 45 | Thr | Thr | Asp | Glu | Leu 50 | Leu | Glu | Leu | Ala | |
| GCG | GCA | GTG | AAT | CCC | GTT | CCG | CCA | GCT | CGT | GAA | ATG | GAT | ATG | CTC | CTG | 426 |
| Ala 55 | Ala | Val | Asn | Pro | Val 60 | Pro | Pro | Ala | Arg | Glu 65 | Met | Asp | Met | Leu | Leu 70 | |
| ACT | GCT | GGT | GAG | CGT | ATT | TCT | AAC | GCT | CTC | GTC | GCC | ATG | GCT | ATT | GAG | 474 |
| Thr | Ala | Gly | Glu | Arg 75 | Ile | Ser | Asn | Ala | Leu 80 | Val | Ala | Met | Ala | Ile 85 | Glu | |
| TCC | CTT | GGC | GCA | GAA | GCT | CAA | TCT | TTC | ACT | GGC | TCT | CAG | GCT | GGT | GTG | 522 |
| Ser | Leu | Gly | Ala 90 | Glu | Ala | Gln | Ser | Phe 95 | Thr | Gly | Ser | Gln | Ala 100 | Gly | Val | |
| CTC | ACC | ACC | GAG | CGC | CAC | GGA | AAC | GCA | CGC | ATT | GTT | GAC | GTC | ACA | CCG | 570 |
| Leu | Thr | Thr 105 | Glu | Arg | His | Gly | Asn 110 | Ala | Arg | Ile | Val | Asp 115 | Val | Thr | Pro | |
| GGT | CGT | GTG | CGT | GAA | GCA | CTC | GAT | GAG | GGC | AAG | ATC | TGC | ATT | GTT | GCT | 618 |
| Gly | Arg 120 | Val | Arg | Glu | Ala | Leu 125 | Asp | Glu | Gly | Lys | Ile 130 | Cys | Ile | Val | Ala | |
| GGT | TTT | CAG | GGT | GTT | AAT | AAA | GAA | ACC | CGC | GAT | GTC | ACC | ACG | TTG | GGT | 666 |
| Gly 135 | Phe | Gln | Gly | Val | Asn 140 | Lys | Glu | Thr | Arg | Asp 145 | Val | Thr | Thr | Leu | Gly 150 | |
| CGT | GGT | GGT | TCT | GAC | ACC | ACT | GCA | GTT | GCG | TTG | GCA | GCT | GCT | TTG | AAC | 714 |
| Arg | Gly | Gly | Ser | Asp 155 | Thr | Thr | Ala | Val | Ala 160 | Leu | Ala | Ala | Ala | Leu 165 | Asn | |
| GCT | GAT | GTG | TGT | GAG | ATT | TAC | TCG | GAC | GTT | GAC | GGT | GTG | TAT | ACC | GCT | 762 |
| Ala | Asp | Val | Cys 170 | Glu | Ile | Tyr | Ser | Asp 175 | Val | Asp | Gly | Val | Tyr 180 | Thr | Ala | |
| GAC | CCG | CGC | ATC | GTT | CCT | AAT | GCA | CAG | AAG | CTG | GAA | AAG | CTC | AGC | TTC | 810 |
| Asp | Pro | Arg 185 | Ile | Val | Pro | Asn | Ala 190 | Gln | Lys | Leu | Glu | Lys 195 | Leu | Ser | Phe | |
| GAA | GAA | ATG | CTG | GAA | CTT | GCT | GCT | GTT | GGC | TCC | AAG | ATT | TTG | GTG | CTG | 858 |
| Glu | Glu 200 | Met | Leu | Glu | Leu 205 | Ala | Ala | Val | Gly | Ser 210 | Lys | Ile | Leu | Val | Leu | |
| CGC | AGT | GTT | GAA | TAC | GCT | CGT | GCA | TTC | AAT | GTG | CCA | CTT | CGC | GTA | CGC | 906 |
| Arg 215 | Ser | Val | Glu | Tyr | Ala 220 | Arg | Ala | Phe | Asn | Val 225 | Pro | Leu | Arg | Val | Arg 230 | |
| TCG | TCT | TAT | AGT | AAT | GAT | CCC | GGC | ACT | TTG | ATT | GCC | GGC | TCT | ATG | GAG | 954 |
| Ser | Ser | Tyr | Ser | Asn 235 | Asp | Pro | Gly | Thr | Leu 240 | Ile | Ala | Gly | Ser | Met 245 | Glu | |
| GAT | ATT | CCT | GTG | GAA | GAA | GCA | GTC | CTT | ACC | GGT | GTC | GCA | ACC | GAC | AAG | 1002 |
| Asp | Ile | Pro | Val 250 | Glu | Glu | Ala | Val | Leu 255 | Thr | Gly | Val | Ala | Thr 260 | Asp | Lys | |
| TCC | GAA | GCC | AAA | GTA | ACC | GTT | CTG | GGT | ATT | TCC | GAT | AAG | CCA | GGC | GAG | 1050 |
| Ser | Glu | Ala | Lys 265 | Val | Thr | Val | Leu | Gly 270 | Ile | Ser | Asp | Lys | Pro 275 | Gly | Glu | |
| ACT | GCC | AAG | GTT | TTC | CGT | GCG | TTG | GCT | GAT | GCA | GAA | ATC | AAC | ATT | GAC | 1098 |
| Thr | Ala | Lys 280 | Val | Phe | Arg | Ala | Leu 285 | Ala | Asp | Ala | Glu | Ile 290 | Asn | Ile | Asp | |
| ATG | GTT | CTG | CAG | AAC | GTC | TCC | TCT | GTG | GAA | GAC | GGC | ACC | ACC | GAC | ATC | 1146 |
| Met | Val 295 | Leu | Gln | Asn | Val | Ser 300 | Ser | Val | Glu | Asp 305 | Gly | Thr | Thr | Asp | Ile 310 | |
| ACG | TTC | ACC | TGC | CCT | CGC | GCT | GAC | GGA | CGC | CGT | GCG | ATG | GAG | ATC | TTG | 1194 |
| Thr | Phe | Thr | Cys 315 | Pro | Arg | Ala | Asp | Gly 320 | Arg | Arg | Ala | Met | Glu 325 | Ile | Leu | |
| AAG | AAG | CTT | CAG | GTT | CAG | GGC | AAC | TGG | ACC | AAT | GTG | CTT | TAC | GAC | GAC | 1242 |
| Lys | Lys | Leu | Gln 330 | Val | Gln | Gly | Asn | Trp 335 | Thr | Asn | Val | Leu | Tyr 340 | Asp | Asp | |

| | | | | | | | | | | | | | | | | |
|---|---|---|---|---|---|---|---|---|---|---|---|---|---|---|---|---|
| CAG | GTC | GGC | AAA | GTC | TCC | CTC | GTG | GGT | GCT | GGC | ATG | AAG | TCT | CAC | CCA | 1290 |
| Gln | Val | Gly | Lys | Val | Ser | Leu | Val | Gly | Ala | Gly | Met | Lys | Ser | His | Pro | |
| | | 345 | | | | 350 | | | | | 355 | | | | | |
| GGT | GTT | ACC | GCA | GAG | TTC | ATG | GAA | GCT | CTG | CGC | GAT | GTC | AAC | GTG | AAC | 1338 |
| Gly | Val | Thr | Ala | Glu | Phe | Met | Glu | Ala | Leu | Arg | Asp | Val | Asn | Val | Asn | |
| | 360 | | | | | 365 | | | | | 370 | | | | | |
| ATC | GAA | TTG | ATT | TCC | ACC | TCT | GAG | ATC | CGC | ATT | TCC | GTG | CTG | ATC | CGT | 1386 |
| Ile | Glu | Leu | Ile | Ser | Thr | Ser | Glu | Ile | Arg | Ile | Ser | Val | Leu | Ile | Arg | |
| 375 | | | | | 380 | | | | | 385 | | | | | 390 | |
| GAA | GAT | GAT | CTG | GAT | GCT | GCT | GCA | CGT | GCA | TTG | CAT | GAG | CAG | TTC | CAG | 1434 |
| Glu | Asp | Asp | Leu | Asp | Ala | Ala | Ala | Arg | Ala | Leu | His | Glu | Gln | Phe | Gln | |
| | | | | 395 | | | | 400 | | | | | | 405 | | |
| CTG | GGC | GGC | GAA | GAC | GAA | GCC | GTC | GTT | TAT | GCA | GGC | ACC | GGA | CGC | TAA | 1482 |
| Leu | Gly | Gly | Glu | Asp | Glu | Ala | Val | Val | Tyr | Ala | Gly | Thr | Gly | Arg | | |
| | | | 410 | | | | | 415 | | | | | 420 | 421 | | |

AGTTTTAAAG GAGTAGTTTT ACAATGACCA CCATCGCAGT TGTTGGTGCA ACCGGCCAGG   1542

TCGGCCAGGT TATGCGCACC CTTTTGGAAG AGCGCAATTT CCCAGCTGAC ACTGTTCGTT   1602

TCTTTGCTTC CCCGCGTTCC GCAGGCCGTA AGATTGAATT C                      1643

( 2 ) INFORMATION FOR SEQ ID NO:9:

( i ) SEQUENCE CHARACTERISTICS:
        ( A ) LENGTH: 1643 nucleotides
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
        ( A ) ORGANISM: Corynebacterium glutamicum
        ( B ) STRAIN: ATCC13869

( i x ) FEATURE:
        ( A ) NAME/KEY: mat peptide
        ( B ) LOCATION: 964..1482

( x i ) SEQUENCE DESCRIPTION: SEQ ID NO:9:

TCGCGAAGTA GCACCTGTCA CTTTTGTCTC AAATATTAAA TCGAATATCA ATATACGGTC    60

TGTTTATTGG AACGCATCCC AGTGGCTGAG ACGCATCCGC TAAAGCCCCA GGAACCCTGT   120

GCAGAAAGAA AACACTCCTC TGGCTAGGTA GACACAGTTT ATAAAGGTAG AGTTGAGCGG   180

GTAACTGTCA GCACGTAGAT CGAAAGGTGC ACAAAGGTGG CCCTGGTCGT ACAGAAATAT   240

GGCGGTTCCT CGCTTGAGAG TGCGGAACGC ATTAGAAACG TCGCTGAACG GATCGTTGCC   300

ACCAAGAAGG CTGGAAATGA TGTCGTGGTT GTCTGCTCCG CAATGGGAGA CACCACGGAT   360

GAACTTCTAG AACTTGCAGC GGCAGTGAAT CCCGTTCCGC CAGCTCGTGA AATGGATATG   420

CTCCTGACTG CTGGTGAGCG TATTTCTAAC GCTCTCGTCG CCATGGCTAT TGAGTCCCTT   480

GGCGCAGAAG CTCAATCTTT CACTGGCTCT CAGGCTGGTG TGCTCACCAC CGAGCGCCAC   540

GGAAACGCAC GCATTGTTGA CGTCACACCG GGTCGTGTGC GTGAAGCACT CGATGAGGGC   600

AAGATCTGCA TTGTTGCTGG TTTTCAGGGT GTTAATAAAG AAACCCGCGA TGTCACCACG   660

TTGGGTCGTG GTGGTTCTGA CACCACTGCA GTTGCGTTGG CAGCTGCTTT GAACGCTGAT   720

GTGTGTGAGA TTTACTCGGA CGTTGACGGT GTGTATACCG CTGACCCGCG CATCGTTCCT   780

AATGCACAGA AGCTGGAAAA GCTCAGCTTC GAAGAAATGC TGGAACTTGC TGCTGTTGGC   840

TCCAAGATTT TGGTGCTGCG CAGTGTTGAA TACGCTCGTG CATTCAATGT GCCACTTCGC   900

-continued

```
GTACGCTCGT CTTATAGTAA TGATCCCGGC ACTTTGATTG CCGGCTCTAT GGAGGATATT    960
```

| | | | | | | | | | | | | | | | | |
|---|---|---|---|---|---|---|---|---|---|---|---|---|---|---|---|---|
| CCT | GTG | GAA | GAA | GCA | GTC | CTT | ACC | GGT | GTC | GCA | ACC | GAC | AAG | TCC | GAA | 1008 |
| Met | Glu | Glu | Ala | Val | Leu | Thr | Gly | Val | Ala | Thr | Asp | Lys | Ser | Glu | | |
| 1 | | | | 5 | | | | | 10 | | | | | 15 | | |
| GCC | AAA | GTA | ACC | GTT | CTG | GGT | ATT | TCC | GAT | AAG | CCA | GGC | GAG | GCT | GCC | 1056 |
| Ala | Lys | Val | Thr | Val | Leu | Gly | Ile | Ser | Asp | Lys | Pro | Gly | Glu | Ala | Ala | |
| | | 20 | | | | | 25 | | | | | 30 | | | | |
| AAG | GTT | TTC | CGT | GCG | TTG | GCT | GAT | GCA | GAA | ATC | AAC | ATT | GAC | ATG | GTT | 1104 |
| Lys | Val | Phe | Arg | Ala | Leu | Ala | Asp | Ala | Glu | Ile | Asn | Ile | Asp | Met | Val | |
| | | | 35 | | | | | 40 | | | | | 45 | | | |
| CTG | CAG | AAC | GTC | TCC | TCT | GTG | GAA | GAC | GGC | ACC | ACC | GAC | ATC | ACG | TTC | 1152 |
| Leu | Gln | Asn | Val | Ser | Ser | Val | Glu | Asp | Gly | Thr | Thr | Asp | Ile | Thr | Phe | |
| | | 50 | | | | | 55 | | | | | 60 | | | | |
| ACC | TGC | CCT | CGC | GCT | GAC | GGA | CGC | CGT | GCG | ATG | GAG | ATC | TTG | AAG | AAG | 1200 |
| Thr | Cys | Pro | Arg | Ala | Asp | Gly | Arg | Arg | Ala | Met | Glu | Ile | Leu | Lys | Lys | |
| | 65 | | | | | 70 | | | | | 75 | | | | | |
| CTT | CAG | GTT | CAG | GGC | AAC | TGG | ACC | AAT | GTG | CTT | TAC | GAC | GAC | CAG | GTC | 1248 |
| Leu | Gln | Val | Gln | Gly | Asn | Trp | Thr | Asn | Val | Leu | Tyr | Asp | Asp | Gln | Val | |
| 80 | | | | | 85 | | | | | 90 | | | | | 95 | |
| GGC | AAA | GTC | TCC | CTC | GTG | GGT | GCT | GGC | ATG | AAG | TCT | CAC | CCA | GGT | GTT | 1296 |
| Gly | Lys | Val | Ser | Leu | Val | Gly | Ala | Gly | Met | Lys | Ser | His | Pro | Gly | Val | |
| | | | | 100 | | | | | 105 | | | | | 110 | | |
| ACC | GCA | GAG | TTC | ATG | GAA | GCT | CTG | CGC | GAT | GTC | AAC | GTG | AAC | ATC | GAA | 1344 |
| Thr | Ala | Glu | Phe | Met | Glu | Ala | Leu | Arg | Asp | Val | Asn | Val | Asn | Ile | Glu | |
| | | | 115 | | | | | 120 | | | | | 125 | | | |
| TTG | ATT | TCC | ACC | TCT | GAG | ATC | CGC | ATT | TCC | GTG | CTG | ATC | CGT | GAA | GAT | 1392 |
| Leu | Ile | Ser | Thr | Ser | Glu | Ile | Arg | Ile | Ser | Val | Leu | Ile | Arg | Glu | Asp | |
| | | 130 | | | | | 135 | | | | | 140 | | | | |
| GAT | CTG | GAT | GCT | GCT | GCA | CGT | GCA | TTG | CAT | GAG | CAG | TTC | CAG | CTG | GGC | 1440 |
| Asp | Leu | Asp | Ala | Ala | Ala | Arg | Ala | Leu | His | Glu | Gln | Phe | Gln | Leu | Gly | |
| | 145 | | | | | 150 | | | | | 155 | | | | | |
| GGC | GAA | GAC | GAA | GCC | GTC | GTT | TAT | GCA | GGC | ACC | GGA | CGC | TAAAGTTTTAA | | | 1490 |
| Gly | Glu | Asp | Glu | Ala | Val | Val | Tyr | Ala | Gly | Thr | Gly | Arg | | | | |
| 160 | | | | | 165 | | | | | 170 | | 172 | | | | |

```
AGGAGTAGTT TTACAATGAC CACCATCGCA GTTGTTGGTG CAACCGGCCA GGTCGGCCAG    1550

GTTATGCGCA CCCTTTTGGA AGAGCGCAAT TTCCCAGCTG ACACTGTTCG TTTCTTTGCT    1610

TCCCCGCGTT CCGCAGGCCG TAAGATTGAA TTC                                 1643
```

( 2 ) INFORMATION FOR SEQ ID NO:10:

( i ) SEQUENCE CHARACTERISTICS:
        ( A ) LENGTH: 1643 nucleotides
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
        ( A ) ORGANISM: Corynebacterium glutamicum
        ( B ) STRAIN: AJ3463

( i x ) FEATURE:
        ( A ) NAME/KEY: mat peptide
        ( B ) LOCATION: 964..1482

( x i ) SEQUENCE DESCRIPTION: SEQ ID NO:10:

```
TCGCGAAGTA GCACCTGTCA CTTTTGTCTC AAATATTAAA TCGAATATCA ATATACGGTC    60
```

```
TGTTTATTGG AACGCATCCC AGTGGCTGAG ACGCATCCGC TAAAGCCCCA GGAACCCTGT         120

GCAGAAAGAA AACACTCCTC TGGCTAGGTA GACACAGTTT ATAAAGGTAG AGTTGAGCGG         180

GTAACTGTCA GCACGTAGAT CGAAAGGTGC ACAAGGTGG CCCTGGTCGT ACAGAAATAT          240

GGCGGTTCCT CGCTTGAGAG TGCGGAACGC ATTAGAAACG TCGCTGAACG GATCGTTGCC         300

ACCAAGAAGG CTGGAAATGA TGTCGTGGTT GTCTGCTCCG CAATGGGAGA CACCACGGAT         360

GAACTTCTAG AACTTGCAGC GGCAGTGAAT CCCGTTCCGC CAGCTCGTGA AATGGATATG         420

CTCCTGACTG CTGGTGAGCG TATTTCTAAC GCTCTCGTCG CCATGGCTAT TGAGTCCCTT         480

GGCGCAGAAG CTCAATCTTT CACTGGCTCT CAGGCTGGTG TGCTCACCAC CGAGCGCCAC         540

GGAAACGCAC GCATTGTTGA CGTCACACCG GGTCGTGTGC GTGAAGCACT CGATGAGGGC         600

AAGATCTGCA TTGTTGCTGG TTTTCAGGGT GTTAATAAAG AAACCCGCGA TGTCACCACG         660

TTGGGTCGTG GTGGTTCTGA CACCACTGCA GTTGCGTTGG CAGCTGCTTT GAACGCTGAT         720

GTGTGTGAGA TTTACTCGGA CGTTGACGGT GTGTATACCG CTGACCCGCG CATCGTTCCT         780

AATGCACAGA AGCTGGAAAA GCTCAGCTTC GAAGAAATGC TGGAACTTGC TGCTGTTGGC         840

TCCAAGATTT TGGTGCTGCG CAGTGTTGAA TACGCTCGTG CATTCAATGT GCCACTTCGC         900

GTACGCTCGT CTTATAGTAA TGATCCCGGC ACTTTGATTG CCGGCTCTAT GGAGGATATT         960

CCT GTG GAA GAA GCA GTC CTT ACC GGT GTC GCA ACC GAC AAG TCC GAA         1008
    Val Glu Glu Ala Val Leu Thr Gly Val Ala Thr Asp Lys Ser Glu
    1               5                   10                  15

GCC AAA GTA ACC GTT CTG GGT ATT TCC GAT AAG CCA GGC GAG ACT GCC         1056
Ala Lys Val Thr Val Leu Gly Ile Ser Asp Lys Pro Gly Glu Thr Ala
                20                  25                  30

AAG GTT TTC CGT GCG TTG GCT GAT GCA GAA ATC AAC ATT GAC ATG GTT         1104
Lys Val Phe Arg Ala Leu Ala Asp Ala Glu Ile Asn Ile Asp Met Val
            35                  40                  45

CTG CAG AAC GTC TCC TCT GTG GAA GAC GGC ACC ACC GAC ATC ACG TTC         1152
Leu Gln Asn Val Ser Ser Val Glu Asp Gly Thr Thr Asp Ile Thr Phe
        50                  55                  60

ACC TGC CCT CGC GCT GAC GGA CGC CGT GCG ATG GAG ATC TTG AAG AAG         1200
Thr Cys Pro Arg Ala Asp Gly Arg Arg Ala Met Glu Ile Leu Lys Lys
65                  70                  75

CTT CAG GTT CAG GGC AAC TGG ACC AAT GTG CTT TAC GAC GAC CAG GTC         1248
Leu Gln Val Gln Gly Asn Trp Thr Asn Val Leu Tyr Asp Asp Gln Val
80                  85                  90                      95

GGC AAA GTC TCC CTC GTG GGT GCT GGC ATG AAG TCT CAC CCA GGT GTT         1296
Gly Lys Val Ser Leu Val Gly Ala Gly Met Lys Ser His Pro Gly Val
            100                 105                 110

ACC GCA GAG TTC ATG GAA GCT CTG CGC GAT GTC AAC GTG AAC ATC GAA         1344
Thr Ala Glu Phe Met Glu Ala Leu Arg Asp Val Asn Val Asn Ile Glu
        115                 120                 125

TTG ATT TCC ACC TCT GAG ATC CGC ATT TCC GTG CTG ATC CGT GAA GAT         1392
Leu Ile Ser Thr Ser Glu Ile Arg Ile Ser Val Leu Ile Arg Glu Asp
        130                 135                 140

GAT CTG GAT GCT GCT GCA CGT GCA TTG CAT GAG CAG TTC CAG CTG GGC         1440
Asp Leu Asp Ala Ala Ala Arg Ala Leu His Glu Gln Phe Gln Leu Gly
        145                 150                 155

GGC GAA GAC GAA GCC GTC GTT TAT GCA GGC ACC GGA CGC TAAAGTTTAA         1490
Gly Glu Asp Glu Ala Val Val Tyr Ala Gly Thr Gly Arg
160                 165                 170     172

AGGAGTAGTT TTACAATGAC CACCATCGCA GTTGTTGGTG CAACCGGCCA GGTCGGCCAG         1550

GTTATGCGCA CCCTTTTGGA AGAGCGCAAT TTCCCAGCTG ACACTGTTCG TTTCTTTGCT         1610

TCCCCGCGTT CCGCAGGCCG TAAGATTGAA TTC                                     1643
```

( 2 ) INFORMATION FOR SEQ ID NO:11:

( i ) SEQUENCE CHARACTERISTICS:
        ( A ) LENGTH: 1263 nucleotides
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
        ( A ) ORGANISM: Corynebacterium glutamicum
        ( B ) STRAIN: ATCC13869

( x i ) SEQUENCE DESCRIPTION: SEQ ID NO:11:

```
GTGGCCCTGG TCGTACAGAA ATATGGCGGT TCCTCGCTTG AGAGTGCGGA ACGCATTAGA    60
AACGTCGCTG AACGGATCGT TGCCACCAAG AAGGCTGGAA ATGATGTCGT GGTTGTCTGC   120
TCCGCAATGG GAGACACCAC GGATGAACTT CTAGAACTTG CAGCGGCAGT GAATCCCGTT   180
CCGCCAGCTC GTGAAATGGA TATGCTCCTG ACTGCTGGTG AGCGTATTTC TAACGCTCTC   240
GTCGCCATGG CTATTGAGTC CCTTGGCGCA GAAGCTCAAT CTTTCACTGG CTCTCAGGCT   300
GGTGTGCTCA CCACCGAGCG CCACGGAAAC GCACGCATTG TTGACGTCAC ACCGGGTCGT   360
GTGCGTGAAG CACTCGATGA GGGCAAGATC TGCATTGTTG CTGGTTTTCA GGGTGTTAAT   420
AAAGAAACCC GCGATGTCAC CACGTTGGGT CGTGGTGGTT CTGACACCAC TGCAGTTGCG   480
TTGGCAGCTG CTTTGAACGC TGATGTGTGT GAGATTTACT CGGACGTTGA CGGTGTGTAT   540
ACCGCTGACC CGCGCATCGT TCCTAATGCA CAGAAGCTGG AAAAGCTCAG CTTCGAAGAA   600
ATGCTGGAAC TTGCTGCTGT TGGCTCCAAG ATTTTGGTGC TGCGCAGTGT TGAATACGCT   660
CGTGCATTCA ATGTGCCACT TCGCGTACGC TCGTCTTATA GTAATGATCC CGGCACTTTG   720
ATTGCCGGCT CTATGGAGGA TATTCCTGTG GAAGAAGCAG TCCTTACCGG TGTCGCAACC   780
GACAAGTCCG AAGCCAAAGT AACCGTTCTG GGTATTTCCG ATAAGCCAGG CGAGGCTGCC   840
AAGGTTTTCC GTGCGTTGGC TGATGCAGAA ATCAACATTG ACATGGTTCT GCAGAACGTC   900
TCCTCTGTGG AAGACGGCAC CACCGACATC ACGTTCACCT GCCCTCGCGC TGACGGACGC   960
CGTGCGATGG AGATCTTGAA GAAGCTTCAG GTTCAGGGCA ACTGGACCAA TGTGCTTTAC  1020
GACGACCAGG TCGGCAAAGT CTCCCTCGTG GGTGCTGGCA TGAAGTCTCA CCCAGGTGTT  1080
ACCGCAGAGT TCATGGAAGC TCTGCGCGAT GTCAACGTGA ACATCGAATT GATTTCCACC  1140
TCTGAGATCC GCATTTCCGT GCTGATCCGT GAAGATGATC TGGATGCTGC TGCACGTGCA  1200
TTGCATGAGC AGTTCCAGCT GGGCGGCGAA GACGAAGCCG TCGTTTATGC AGGCACCGGA  1260
CGC                                                                1263
```

( 2 ) INFORMATION FOR SEQ ID NO:12:

( i ) SEQUENCE CHARACTERISTICS:
        ( A ) LENGTH: 1263 nucleotides
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: NO ( i v ) ANTI-SENSE: NO (v i) ORIGINAL SOURCE:
    (A) ORGANISM: Corynebacterium glutamicum
    (B) STRAIN: AJ3463

(x i) SEQUENCE DESCRIPTION: SEQ ID NO:12:

```
GTGGCCCTGG  TCGTACAGAA  ATATGGCGGT  TCCTCGCTTG  AGAGTGCGGA  ACGCATTAGA    60
AACGTCGCTG  AACGGATCGT  TGCCACCAAG  AAGGCTGGAA  ATGATGTCGT  GGTTGTCTGC   120
TCCGCAATGG  GAGACACCAC  GGATGAACTT  CTAGAACTTG  CAGCGGCAGT  GAATCCCGTT   180
CCGCCAGCTC  GTGAAATGGA  TATGCTCCTG  ACTGCTGGTG  AGCGTATTTC  TAACGCTCTC   240
GTCGCCATGG  CTATTGAGTC  CCTTGGCGCA  GAAGCTCAAT  CTTTCACTGG  CTCTCAGGCT   300
GGTGTGCTCA  CCACCGAGCG  CCACGGAAAC  GCACGCATTG  TTGACGTCAC  ACCGGGTCGT   360
GTGCGTGAAG  CACTCGATGA  GGGCAAGATC  TGCATTGTTG  CTGGTTTTCA  GGGTGTTAAT   420
AAAGAAACCC  GCGATGTCAC  CACGTTGGGT  CGTGGTGGTT  CTGACACCAC  TGCAGTTGCG   480
TTGGCAGCTG  CTTTGAACGC  TGATGTGTGT  GAGATTTACT  CGGACGTTGA  CGGTGTGTAT   540
ACCGCTGACC  CGCGCATCGT  TCCTAATGCA  CAGAAGCTGG  AAAAGCTCAG  CTTCGAAGAA   600
ATGCTGGAAC  TTGCTGCTGT  TGGCTCCAAG  ATTTTGGTGC  TGCGCAGTGT  TGAATACGCT   660
CGTGCATTCA  ATGTGCCACT  TCGCGTACGC  TCGTCTTATA  GTAATGATCC  CGGCACTTTG   720
ATTGCCGGCT  CTATGGAGGA  TATTCCTGTG  GAAGAAGCAG  TCCTTACCGG  TGTCGCAACC   780
GACAAGTCCG  AAGCCAAAGT  AACCGTTCTG  GGTATTTCCG  ATAAGCCAGG  CGAGACTGCC   840
AAGGTTTTCC  GTGCGTTGGC  TGATGCAGAA  ATCAACATTG  ACATGGTTCT  GCAGAACGTC   900
TCCTCTGTGG  AAGACGGCAC  CACCGACATC  ACGTTCACCT  GCCCTCGCGC  TGACGGACGC   960
CGTGCGATGG  AGATCTTGAA  GAAGCTTCAG  GTTCAGGGCA  ACTGGACCAA  TGTGCTTTAC  1020
GACGACCAGG  TCGGCAAAGT  CTCCCTCGTG  GGTGCTGGCA  TGAAGTCTCA  CCCAGGTGTT  1080
ACCGCAGAGT  TCATGGAAGC  TCTGCGCGAT  GTCAACGTGA  ACATCGAATT  GATTTCCACC  1140
TCTGAGATCC  GCATTTCCGT  GCTGATCCGT  GAAGATGATC  TGGATGCTGC  TGCACGTGCA  1200
TTGCATGAGC  AGTTCCAGCT  GGGCGGCGAA  GACGAAGCCG  TCGTTTATGC  AGGCACCGGA  1260
CGC                                                                    1263
```

(2) INFORMATION FOR SEQ ID NO:13:

(i) SEQUENCE CHARACTERISTICS:
        (A) LENGTH: 516 nucleotides
        (B) TYPE: nucleic acid
        (C) STRANDEDNESS: double
        (D) TOPOLOGY: linear (i i) MOLECULE TYPE: genomic DNA (i i i) HYPOTHETICAL: NO (i v) ANTI-SENSE: NO (v i) ORIGINAL SOURCE:
        (A) ORGANISM: Corynebacterium glutamicum
        (B) STRAIN: ATCC13869

(x i) SEQUENCE DESCRIPTION: SEQ ID NO:13:

```
GTGGAAGAAG  CAGTCCTTAC  CGGTGTCGCA  ACCGACAAGT  CCGAAGCCAA  AGTAACCGTT    60
CTGGGTATTT  CCGATAAGCC  AGGCGAGGCT  GCCAAGGTTT  TCCGTGCGTT  GGCTGATGCA   120
GAAATCAACA  TTGACATGGT  TCTGCAGAAC  GTCTCCTCTG  TGGAAGACGG  CACCACCGAC   180
ATCACGTTCA  CCTGCCCTCG  CGCTGACGGA  CGCCGTGCGA  TGGAGATCTT  GAAGAAGCTT   240
CAGGTTCAGG  GCAACTGGAC  CAATGTGCTT  TACGACGACC  AGGTCGGCAA  AGTCTCCCTC   300
```

```
GTGGGTGCTG  GCATGAAGTC  TCACCCAGGT  GTTACCGCAG  AGTTCATGGA  AGCTCTGCGC    360

GATGTCAACG  TGAACATCGA  ATTGATTTCC  ACCTCTGAGA  TCCGCATTTC  CGTGCTGATC    420

CGTGAAGATG  ATCTGGATGC  TGCTGCACGT  GCATTGCATG  AGCAGTTCCA  GCTGGGCGGC    480

GAAGACGAAG  CCGTCGTTTA  TGCAGGCACC  GGACGC                                516
```

( 2 ) INFORMATION FOR SEQ ID NO:14:

( i ) SEQUENCE CHARACTERISTICS:
        ( A ) LENGTH: 516 nucleotides
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
        ( A ) ORGANISM: Corynebacterium glutamicum
        ( B ) STRAIN: AJ3463

( x i ) SEQUENCE DESCRIPTION: SEQ ID NO:14:

```
GTGGAAGAAG  CAGTCCTTAC  CGGTGTCGCA  ACCGACAAGT  CCGAAGCCAA  AGTAACCGTT     60

CTGGGTATTT  CCGATAAGCC  AGGCGAGACT  GCCAAGGTTT  TCCGTGCGTT  GGCTGATGCA    120

GAAATCAACA  TTGACATGGT  TCTGCAGAAC  GTCTCCTCTG  TGGAAGACGG  CACCACCGAC    180

ATCACGTTCA  CCTGCCCTCG  CGCTGACGGA  CGCCGTGCGA  TGGAGATCTT  GAAGAAGCTT    240

CAGGTTCAGG  GCAACTGGAC  CAATGTGCTT  TACGACGACC  AGGTCGGCAA  AGTCTCCCTC    300

GTGGGTGCTG  GCATGAAGTC  TCACCCAGGT  GTTACCGCAG  AGTTCATGGA  AGCTCTGCGC    360

GATGTCAACG  TGAACATCGA  ATTGATTTCC  ACCTCTGAGA  TCCGCATTTC  CGTGCTGATC    420

CGTGAAGATG  ATCTGGATGC  TGCTGCACGT  GCATTGCATG  AGCAGTTCCA  GCTGGGCGGC    480

GAAGACGAAG  CCGTCGTTTA  TGCAGGCACC  GGACGC                                516
```

( 2 ) INFORMATION FOR SEQ ID NO:15:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:15:

```
TCGCGAAGTA  GCACCTGTCA  CTT                                                23
```

( 2 ) INFORMATION FOR SEQ ID NO:16:

( i ) SEQUENCE CHARACTERISTICS:
        ( A ) LENGTH: 21 nucleotides
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:16:

```
ACGGAATTCA  ATCTTACGGC  C                                                  21
```

( 2 ) INFORMATION FOR SEQ ID NO:17:

( i ) SEQUENCE CHARACTERISTICS:
  ( A ) LENGTH: 23 nucleotides
  ( B ) TYPE: nucleic acid
  ( C ) STRANDEDNESS: single
  ( D ) TOPOLOGY: linear ( i i ) MOLECULE TYPE: synthetic DNA ( x i ) SEQUENCE DESCRIPTION: SEQ ID NO:17:

GCCAGGCGAG CGTGCCAAGG TTT     23

( 2 ) INFORMATION FOR SEQ ID NO:18:

( i ) SEQUENCE CHARACTERISTICS:
    ( A ) LENGTH: 23 nucleotides
    ( B ) TYPE: nucleic acid
    ( C ) STRANDEDNESS: single
    ( D ) TOPOLOGY: linear ( i i ) MOLECULE TYPE: synthetic DNA ( x i ) SEQUENCE DESCRIPTION: SEQ ID NO:18:

GCCAGGCGAG GATGCCAAGG TTT     23

( 2 ) INFORMATION FOR SEQ ID NO:19:

( i ) SEQUENCE CHARACTERISTICS:
    ( A ) LENGTH: 23 nucleotides
    ( B ) TYPE: nucleic acid
    ( C ) STRANDEDNESS: single
    ( D ) TOPOLOGY: linear ( i i ) MOLECULE TYPE: synthetic DNA ( x i ) SEQUENCE DESCRIPTION: SEQ ID NO:19:

GCCAGGCGAG TGTGCCAAGG TTT     23

( 2 ) INFORMATION FOR SEQ ID NO:20:

( i ) SEQUENCE CHARACTERISTICS:
    ( A ) LENGTH: 23 nucleotides
    ( B ) TYPE: nucleic acid
    ( C ) STRANDEDNESS: single
    ( D ) TOPOLOGY: linear ( i i ) MOLECULE TYPE: synthetic DNA ( x i ) SEQUENCE DESCRIPTION: SEQ ID NO:20:

GCCAGGCGAG TTTGCCAAGG TTT     23

( 2 ) INFORMATION FOR SEQ ID NO:21:

( i ) SEQUENCE CHARACTERISTICS:
    ( A ) LENGTH: 23 nucleotides
    ( B ) TYPE: nucleic acid
    ( C ) STRANDEDNESS: single
    ( D ) TOPOLOGY: linear ( i i ) MOLECULE TYPE: synthetic DNA ( x i ) SEQUENCE DESCRIPTION: SEQ ID NO:21:

GCCAGGCGAG CCTGCCAAGG TTT     23

( 2 ) INFORMATION FOR SEQ ID NO:22:

( i ) SEQUENCE CHARACTERISTICS:
    ( A ) LENGTH: 23 nucleotides
    ( B ) TYPE: nucleic acid
    ( C ) STRANDEDNESS: single -continued ( D ) TOPOLOGY: linear ( i i ) MOLECULE TYPE: synthetic DNA ( x i ) SEQUENCE DESCRIPTION: SEQ ID NO:22:

GCCAGGCGAG TCTGCCAAGG TTT    23

( 2 ) INFORMATION FOR SEQ ID NO:23:

( i ) SEQUENCE CHARACTERISTICS:
      ( A ) LENGTH: 23 nucleotides
      ( B ) TYPE: nucleic acid
      ( C ) STRANDEDNESS: single
      ( D ) TOPOLOGY: linear ( i i ) MOLECULE TYPE: synthetic DNA ( x i ) SEQUENCE DESCRIPTION: SEQ ID NO:23:

GCCAGGCGAG TATGCCAAGG TTT    23

( 2 ) INFORMATION FOR SEQ ID NO:24:

( i ) SEQUENCE CHARACTERISTICS:
      ( A ) LENGTH: 23 nucleotides
      ( B ) TYPE: nucleic acid
      ( C ) STRANDEDNESS: single
      ( D ) TOPOLOGY: linear ( i i ) MOLECULE TYPE: synthetic DNA ( x i ) SEQUENCE DESCRIPTION: SEQ ID NO:24:

GCCAGGCGAG GTTGCCAAGG TTT    23

MUTANT ASPARTOKINASE GENE

TECHNICAL FIELD

The present invention relates to a novel aspartokinase and a DNA fragment coding for the enzyme originating from a bacterium belonging to the genus Corynebacterium used for fermentative production of amino acid and so on, and relates to recombinant DNA containing the DNA fragment. The present invention also relates to a bacterium belonging to the genus Corynebacterium harboring the recombinant DNA, and relates to a method of producing L-lysine comprising cultivating the microorganism.

BACKGROUND ART

L-Lysine, which is used as a feed additive, is usually produced by fermentation by using an L-lysine-producing mutant strain belonging to coryneform bacteria. A variety of L-lysine-producing bacteria are known at present, which are those created by artificial mutation of coryneform bacteria. Such artificial mutant strains includes the followings: S-(2-aminoethyl)cysteine (hereinafter abbreviated as "AEC") resistant mutant strains; mutant strains which require amino acid such as L-homoserine for their growth (Japanese Patent Publication Nos. 48-28078 and 56-6499); mutant strains which exhibit resistance to AEC and require amino acids such as L-leucine, L-homoserine, L-proline, L-serine, L-arginine, L-alanine, and L-valine (U.S. Pat. Nos. 3,708,395 and 3,825,472); L-lysine-producing mutant strains which exhibit resistance to DL-α-amino-ε-caprolactam, α-amino-lauryllactam, aspartic acid-analog, sulfa drug, quinoid, and N-lauroylleucine; L-lysine-producing mutant strains which exhibit resistance to inhibitors of oxyaloacetate decarboxylase or respiratory system enzymes (Japanese Patent Laid-open Nos. 50-53588, 50-31093, 52-102498, 53-9394, 53-86089, 55-9783, 55-9759, 56-32995 and 56-39778, and Japanese Patent Publication Nos. 53-43591 and 53-1833); L-lysine-producing mutant strains which require inositol or acetic acid (Japanese Patent Laid-open Nos. 55-9784 and 56-8692); L-lysine-producing mutant strains which exhibit sensitivity to fluoropyruvic acid or temperature not less than 34° C. (Japanese Patent Laid-open Nos. 55-9783 and 53-86090); and mutant strains belonging to the genus Brevibacterium or Corynebacterium which exhibit resistance to ethylene glycol and produce L-lysine (U.S. patent application Ser. No. 333,455).

*Escherichia coli* transformed by using a recombinant vector is disclosed in the prior art. In this strain, amino acid production is enhanced (see U.S. Pat. No. 4,278,765).

In relation to the genera Brevibacterium and Corynebacterium, there are disclosed a vector plasmid which is autonomously replicable in bacterial cells and has a drug resistance marker gene (see U.S. patent application Ser. No. 386,980), and a method for introducing genes into bacterial cells (Japanese Patent Laid-open No. 2-207791). There is disclosed a possibility to breed L-threonine- or L-isoleucine-producing bacteria by using the techniques described above (see U.S. patent application Ser. Nos. 376,396 and 392,145). In relation to breeding of L-lysine-producing bacteria, a technique is known in which a gene relevant to L-lysine biosynthesis is integrated into a vector plasmid to amplify it in bacterial cells (for example, Japanese Patent Laid-open No. 56-160997). However, no prior art is known in which a gene is specified for aspartokinase (hereinafter referred to as "AK"), a mutation point on the AK gene is elucidated so that feedback inhibition by L-lysine and L-threonine is substantially desensitized, and it is elucidated that the mutation directly relates to productivity of L-lysine. Although a mutant AK gene is described in a few cases, the mutant AK gene could not be harbored as a stable plasmid (see Cremer, J. et al.; *Applied and Environmental Microbiology*, June 1991, pp. 1746–1752).

An object of the present invention is to make improvement to provide increased production and secretion speeds of L-lysine by modifying AK as an important enzyme for lysine biosynthesis in microorganisms of bacteria belonging to the genus Corynebacterium into those having a property of desensitization of feedback inhibition by L-lysine and L-threonine and feedback inhibition by L-lysine alone, and increasing their activities.

DISCLOSURE OF THE INVENTION

As a result of diligent studies, the present inventors have succeeded in obtaining mutant AK genes from a bacterium belonging to the genus Corynebacterium, and completed the present invention. Namely, the present invention lies in an aspartokinase α-subunit protein and a DNA fragment coding for the protein originating from a bacterium belonging to the genus Corynebacterium, in which synergistic feedback inhibition by L-lysine and L-threonine is substantially desensitized, the protein having an amino acid sequence defined in SEQ ID NO: 4 in Sequence Listing, or a sequence in which a 279th Thr residue in the amino acid sequence defined in SEQ ID NO: 4 is changed to an amino acid residue other than Ala and other than acidic amino acids. Further, the present invention lies in an aspartokinase β-subunit protein and a DNA fragment coding for the protein originating from a bacterium belonging to the genus Corynebacterium, in which synergistic feedback inhibition by L-lysine and L-threonine is substantially desensitized, the protein having an amino acid sequence defined in SEQ ID NO: 6 in Sequence Listing, or a sequence in which a 30th Thr residue in the amino acid sequence defined in SEQ ID NO: 6 is changed to an amino acid residue other than Ala and other than acidic amino acids.

In another aspect, the present invention lies in recombinant DNA containing the aforementioned DNA fragment and being replicable in microorganisms belonging to the genus Corynebacterium, and a transformant obtained by introducing the recombinant DNA into a microorganism belonging to the genus Corynebacterium, wherein the specific activity of aspartokinase is increased 2–20 times as compared with a parent strain, and synergistic feedback inhibition by L-lysine and L-threonine or feedback inhibition by L-lysine alone exerted on the activity of aspartokinase is substantially desensitized.

In another aspect, the present invention lies in a method of producing L-lysine comprising the steps of cultivating the aforementioned transformant in an appropriate medium, and separating produced L-lysine.

The microorganisms belonging to the genus Corynebacterium referred to in the present invention are a group of microorganisms as defined in *Bergey's Manual of Determinative Bacteriology*, 8th ed., p. 599 (1974), which are aerobic gram-positive rods having no acid resistance and no spore-forming ability. The microorganisms belonging to the genus Corynebacterium referred to in the present invention include bacteria belonging to the genus Brevibacterium having been hitherto classified into the genus Brevibacterium but united as bacteria belonging to the genus Corynebacterium at present, and include bacteria belonging to the genus Brevibacterium closely relative to bacteria belonging to the genus Corynebacterium. Among the microorganisms belonging to the genus Corynebacterium (Brevibacterium) as described above, especially glutamic acid-producing bacteria belonging to the genus Corynebacterium (Brevibacterium) as mentioned below are most preferable in the present invention. Further, some bacteria belonging to the genus Microbacterium are known to accumulate glutamic acid, which can be also used in the present invention.

Examples of wild type strains of glutamic acid-producing bacteria belonging to the genus Corynebacterium (Brevibacterium) include the followings.

| | |
|---|---|
| Corynebacterium acetoacidophilum | ATCC 13870 |
| Corynebacterium acetoglutamicum | ATCC 15806 |
| Corynebacterium callunae | ATCC 15991 |
| Corynebacterium glutamicum | ATCC 13032 |
| | ATCC 13060 |
| (Brevibacterium divaricatum) | ATCC 14020 |
| (Brevibacterium lactofermentum) | ATCC 13869 |
| Corynebacterium lilium | ATCC 15990 |
| Corynebacterium melassecola | ATCC 17965 |
| Brevibacterium saccharolyticum | ATCC 14066 |
| Brevibacterium immariophilum | ATCC 14068 |
| Brevibacterium roseum | ATCC 13825 |
| Brevibacterium flavum | ATCC 13826 |
| Brevibacterium thiogenitalis | ATCC 19240 |
| Microbacterium ammoniaphilum | ATCC 15354 |

The glutamic acid-producing bacteria belonging to the genus Corynebacterium (Brevibacterium) of the present invention also include mutant strains having glutamic acid productivity or having lost glutamic acid productivity, in addition to the wild type strains having glutamic acid productivity as described above.

When a wild type strain is used as a donor for the DNA fragment containing the AK gene, a DNA fragment containing a wild type AK gene can be obtained. The DNA fragment containing the gene for AK in which synergistic feedback inhibition by L-lysine and L-threonine is substantially desensitized can be obtained by using a mutant strain in which synergistic feedback inhibition on the AK activity by L-lysine and L-threonine is substantially desensitized. The mutant strain can be obtained, for example, from a group of cells subjected to an ordinary mutation treatment, ultraviolet light irradiation, or a treatment with a mutating agent such as N-methyl-N'-nitro-N-nitrosoguanidine (NTG). The AK activity can be measured by using a method described in Miyajima, R. et al., The Journal of Biochemistry (1968), 63(2), 139–148.

As for the donor for the DNA fragment containing the AK gene, Corynebacterium glutamicum (Brevibacterium lactofermentum) wild type strain ATCC 13869, and an L-lysine-producing bacterium AJ3463 (FERM P-1987) derived by a mutation treatment from the ATCC 13869 strain are most preferable donors. The wild type AK gene, and the gene coding for aspartokinase in which synergistic feedback inhibition by L-lysine and L-threonine is substantially desensitized (hereinafter referred to as "mutant AK gene") are separated from chromosomal DNA of these bacteria, ligated with a vector autonomously replicable in bacteria belonging to the genus Corynebacterium (Brevibacterium), and introduced into cells of bacteria belonging to the genus Corynebacterium (Brevibacterium).

A method for isolating the AK gene is as follows. At first, a chromosomal gene is extracted from a strain having the AK gene of a bacterium belonging to the genus Corynebacterium (for example, a method of H. Saito and K. Miura, Biochem. Biophys. Acta, 72, 619 (1963) can be used), and it is digested with a suitable restriction enzyme. Subsequently, it is ligated with a vector replicable in cells of bacteria belonging to the genus Corynebacterium. An obtained recombinant vector is used to transform an AK-deficient mutant strain of a microorganism belonging to the genus Corynebacterium. A bacterial stain consequently harboring the AK-producing activity is isolated, from which the AK gene can be separated. A method for deriving the AK-deficient mutant strain is similar for practice to a method for deriving the mutant strain which provides substantially desensitized synergistic feedback inhibition on the AK activity by L-lysine and L-threonine described above.

Upon digestion of the chromosomal gene, the degree of digestion can be controlled by controlling the digestion reaction time and so on. Thus a wide variety of restriction enzymes can be used.

Any vector replicable in cells of bacteria belonging to the genus Corynebacterium can be used as the vector for the present invention. Specifically, it is exemplified by the followings.

(1) pAM330: see Japanese Patent Laid-open No. 58-67699
(2) pHM1519: see Japanese Patent Laid-open No. 58-77895
(3) pAJ655: see Japanese Patent Laid-open No. 58-192900
(4) pAJ611: see the same
(5) pAJ1844: see the same
(6) pCGi: see Japanese Patent Laid-open No. 57-134500
(7) pCG2: see Japanese Patent Laid-open No. 58-35197
(8) pCG4: see Japanese Patent Laid-open No. 57-183799
(9) pCG11: see the same The vector may be cleaved by digestion with a restriction enzyme which digests the DNA at one place, or by partial digestion with a restriction enzyme which digests it at a plurality of places.

The vector is digested with a restriction enzyme used to digest the chromosomal gene, or ligated with oligonucleotides having nucleotide sequences complementary to both ends of the digested fragment of chromosomal DNA and the digested vector respectively. Subsequently, it is subjected to a ligation reaction of the vector and the chromosomal DNA fragment.

Recombinant DNA constructed by ligating the chromosomal DNA with the vector thus obtained can be introduced into a recipient of bacteria belonging to the genus Corynebacterium by using a method in which permeability of DNA is increased by treating recipient cells with calcium chloride as reported for Escherichia coli K-12 (Mandel, M. and Higa, A., J. Mol. Biol., 53, 159 (1970)), or by using a method in which introduction is performed in a proliferating stage (so-called competent cells) so that cells can incorporate DNA as reported for Bacillus subtills (Duncan, C. H., Wilson, G. A. and Young, F. E., Gene, 1, 153 (1977)). Alternatively, recombinant DNA can be introduced into a DNA recipient after converting DNA recipient cells into protoplasts or spheroplasts which easily incorporate recombinant DNA as known for Bacillus subtills, actinomycetes, and yeasts (Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Acad. Sci. U.S.A., 75, 1929 (1978)).

In the protoplast method, a sufficiently high frequency can be obtained even by using the method used for Bacillus subtills described above. It is of course possible to utilize a method in which DNA is incorporated into protoplasts of a bacterium belonging to the genus Corynebacterium in the presence of polyethylene glycol or polyvinyl alcohol and divalent metal ion as described in Japanese Patent Laid-open No. 57-183799. An equivalent result is obtained even by using a method in which incorporation of DNA is facilitated by addition of carboxymethyl cellulose, dextran, Ficoll, Bruronik F68 (Serva) instead of polyethylene glycol or polyvinyl alcohol.

Alternatively, the AK gene can be obtained by amplifying the AK gene by using PCR (polymerase chain reaction; see White, T. J. et al., *Trends Genet.*, 5, 185 (1989)) from chromosomal DNA obtained as described above. DNA primers to be used for the amplification are those complementary to both 3' ends of DNA double strands containing an entire or partial region of the AK gene. When only a partial region of the AK gene is amplified, it is necessary to perform screening from a gene library by using DNA fragments of the region as primers to amplify a DNA fragment containing an entire region. When an entire region is amplified, a DNA fragment containing the AK gene can be recovered by excising an objective band after subjecting the DNA fragment to agarose gel electrophoresis.

For DNA primers, single strand DNA's of 23 mer and 21 mer having sequences of 5'-TCGCGAAGTAGCACCTGTCACTT-3' (SEQ ID NO:15) and 5'-ACGGAATTCAATCTTACGGCC-3' (SEQ ID NO:16) are most suitable to amplify a region of about 1,643 bp coding for the AK gene based on, for example, a sequence known for *Corynebacterium glutamicum* (see *Molecular Microbiology* (1991), 5(5), 1197–1204; *Mol. Gen. Genet.* (1990), 224, 317–324). The DNA can be synthesized in accordance with an ordinary method using a phosphoramidite method (see *Tetrahedron Letters* (1981), 22, 1859) by using a DNA synthesizer Model 380B produced by Applied Biosystems. The PCR can be performed by using DNA Thermal Cycler Model PJ2000 produced by Takara Shuzo Co., Ltd., using Taq DNA polymerase in accordance with a method designated by the supplier.

The amplified AK gene is ligated with the vector proliferative in cells of bacteria belonging to the genus Corynebacterium as described above, and introduced into cells of bacteria belonging to the genus Corynebacterium by using the method as described above.

Hosts in which the obtained AK gene is introduced and amplified to produce lysine include the wild type strains of glutamic acid-producing bacteria belonging to the genus Corynebacterium described above. All bacteria other than the above can be utilized as a host provided that a replication origin for the recombinant DNA constructed herein and the mutant AK gene make their function, the recombinant DNA can be replicated, and the mutant AK activity can be enhanced. The most preferable host is AJ12036 strain (FERM P-7559) which is a wild type strain of *Corynebacterium glutamicum* (*Brevibacterium lactofermentum*).

The transformant harboring the recombinant DNA containing the gene coding for aspartokinase in which synergistic feedback inhibition by L-lysine and L-threonine is substantially desensitized obtained by the method described above is cultivated, and objective L-lysine is produced and accumulated in a culture liquid to collect it.

The medium to be used for L-lysine production is an ordinary medium containing a carbon source, a nitrogen source, inorganic ions and optionally other organic components.

As the carbon source, it is possible to use sugars such as glucose, lactose, galactose, fructose, and starch hydrolysate; alcohols such as glycerol and sorbitol; or organic acids such as fumaric acid, citric acid and succinic acid.

As the nitrogen source, it is possible to use inorganic ammonium salts such as ammonium sulfate, ammonium chloride and ammonium phosphate; organic nitrogen such as soybean hydrolysate; ammonia gas; and aqueous ammonia.

It is desirable to allow required substances such as vitamin $B_1$ and L-homoserine or yeast extract to be contained in appropriate amounts as organic trace nutrient sources. Other than the above, potassium phosphate, magnesium sulfate, iron ion, manganese ion and so on are added in small amounts, if necessary.

Cultivation is preferably carried out under an aerobic condition for 16–72 hours. The cultivation temperature is controlled at 30° C. to 45° C., and pH is controlled at 5–7 during cultivation. Inorganic or organic, acidic or alkaline substances as well as ammonia gas or the like can be used for pH adjustment. Collection of L-lysine from a cultivated liquor can be carried out by combining an ordinary ion exchange resin method, a precipitation method, and other known methods.

BEST MODE FOR CARRYING OUT THE INVENTION

Figure 1:
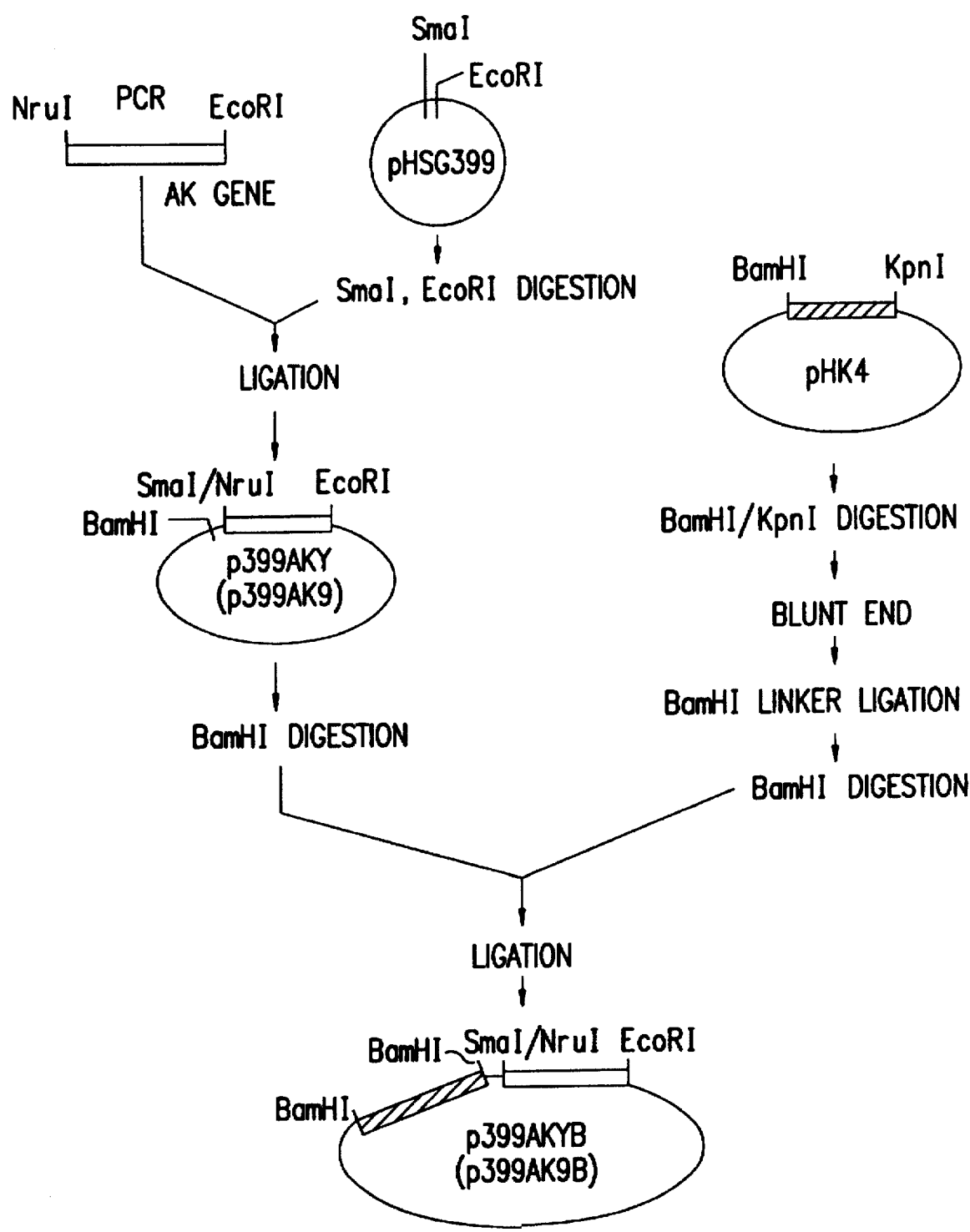
FIG. 1 shows steps of constructing p399AK9 and p399AKY from AK gene fragments amplified from chromosome by PCR, and constructing p399AKYB and p399AK9B by introducing a DNA fragment (Coryne.-ori) having an ability to allow plasmids to be autonomously proliferative in bacteria belonging to the genus Corynebacterium. p399AK9B is constructed through exactly the same steps as those for p399AKYB except that the former is different from the latter in one base. Thus the both are shown together with or without ( ).

The present invention will be concretely explained below with reference to Examples.

Example 1

Preparation of Wild Type and Mutant AK Genes, and Preparation of Plasmids for Corynebacterium Chromosomal DNA was prepared in accordance with an ordinary method from *Corynebacterium glutamicum* (*Brevibacterium lactofermentum*) wild type strain ATCC 13869, and L-lysine-producing mutant strain AJ3463 (FERM P-1987) obtained therefrom by a mutation treatment. AK genes were amplified from the chromosomal DNA by PCR (polymerase chain reaction; see White, T. J. et al., *Trends Genet.*, 5, 185 (1989)). For DNA primers used for the amplification, single strand DNA's of 23 mer and 21 mer having sequences of 5'-TCGCGAAGTAGCACCTGTCACTT-3' (SEQ ID NO: 15) and 5'-ACGGAATTCAATCTTACGGCC-3' (SEQ ID NO: 16) were synthesized to amplify a region of about 1,643 bp coding for the AK genes based on a sequence known for *Corynebacterium glutamicum* (see *Molecular Microbiology* (1991), 5(5), 1197–1204; *Mol. Gen. Genet.* (1990), 224, 317–324). The DNA was synthesized in accordance with an ordinary method using a phosphoramidite method (see *Tetrahedron Letters* (1981), 22, 1859) by using a DNA synthesizer Model 380B produced by Applied Biosystems. In the PCR, the gene was amplified by using DNA Thermal Cycler Model PJ2000 produced by Takara Shuzo Co., Ltd., using Taq DNA polymerase in accordance with a method designated by the supplier. The amplified gene fragment of 1,643 bp was confirmed by agarose gel electrophoresis. Subsequently, the fragment excised from the gel was purified in accordance with an ordinary method, and digested with restriction enzymes NruI (produced by Takara Shuzo) and EcoRI (produced by Takara Shuzo). pHSG399 (see Takeshita, S. et al., *Gene* (1987), 61, 63–74) was used as a vector for cloning the gene fragment. pHSG399 was digested with restriction enzymes SmaI (produced by Takara Shuzo) and EcoRI, and ligated with the amplified AK gene fragment. Ligation of DNA was performed by using DNA ligation kit (produced by Takara Shuzo) in accordance with a designated method. Thus plasmids were prepared in which the AK gene fragments amplified from chromosome of Brevibacterium were ligated with pHSG399. A plasmid having the AK gene originating from ATCC 13869 as a wild type strain was designated as p399AKY, and a plasmid having the AK gene originating from AJ3463 as an L-lysine-producing bacterium was designated as p399AK9.

A DNA fragment having an ability to allow plasmids to be autonomously proliferative in bacteria belonging to the genus Corynebacterium (hereinafter referred to as "Coryne.-ori") was introduced into p399AKY and p399AK9 respectively to prepare plasmids carrying the AK genes autonomously replicable in bacteria belonging to the genus Corynebacterium. In order to obtain Coryne.-ori, a plasmid vector pHK4 autonomously proliferative in bacterial cells of both *Escherichia coli* and bacteria belonging to the genus Corynebacterium was prepared. Some plasmid vectors autonomously proliferative in bacterial cells of both *Escherichia coli* and bacteria belonging to the genus Corynebacterium had been reported. Herein a novel shuttle vector pHK4 was constructed from pAJ1844 (see Japanese Patent Laid-open No. 58-216199) and pHSG298 (see S. Takeshita et al., *Gene*, 61, 63–74 (1987)). pAJ1844 was partially digested with a restriction enzyme Sau3AI, and ligated with pHSG298 having been completely digested with a restriction enzyme BamHI. *Corynebacterium glutamicum* (*Brevibacterium lactofermentum*) AJ12036 (FERM P-7559) was transformed with DNA after the ligation. An electric pulse method (see Japanese Patent Laid-open No. 2-207791) was used for transformation. Transformants were selected on M-CM2G plates containing 25 μg/ml of kanamycin (containing glucose 5 g, polypeptone 10 g, yeast extract 10 g, NaCl 5 g, DL-methionine 0.2 g, and agar 15 g in 1 l of pure water, pH 7.2). Plasmids were prepared from the transformants. One having the smallest size was selected, and designated as pHK4. This plasmid is capable of autonomous proliferation in *Escherichia coli* and bacteria belonging to the genus Corynebacterium, and gives kanamycin resistance to the host.

pHK4 was digested with a restriction enzyme KpnI (produced by Takara Shuzo), and digested ends were blunt-ended. Blunt ends were formed by using DNA Blunting kit (produced by Takara Shuzo) in accordance with a designated method. After the blunt end formation, a phosphorylated BamHI linker (produced by Takara Shuzo) was ligated to make modification so that a DNA fragment of the Coryne.-ori portion could be excised from pHK4 by digestion only with BamHI. This plasmid was digested with BamHI. A generated Coryne.-ori DNA fragment was ligated with p399AKY and p399AK9 having been also digested with BamHI to prepare plasmids being autonomously proliferative in bacteria belonging to the genus Corynebacterium and containing the AK genes. The plasmid containing the wild type AK gene originating from p399AKY was designated as p399AKYB, and the plasmid containing the mutant AK gene originating from p399AK9 was designated as p399AK9B. Steps of constructing p399AK9B and p399AKYB are shown in FIG. 1. A strain AJ12691 obtained by introducing the mutant AK plasmid p399AK9B into AJ12086 strain (FERM P-7559) as a wild type strain of *Corynebacterium glutamicum* (*Brevibacterium divaricatum*) has been awarded a deposition number (FERM P-12918), and deposited in National Institute of Bioscience and Human Technology of Agency of Industrial Science and Technology.

Example 2

Determination of Nucleotide Sequences of Wild Type AK and Mutant AK Genes of *Corynebacterium glutamicum*

The plasmid p399AKY containing the wild type AK gene, and the plasmid p299AK9 containing the mutant AK gene were prepared to determine nucleotide sequences of the wild type and mutant AK genes. Nucleotide sequences were determined in accordance with a method of Sanger (F. Sanger et al., *Proc. Natl. Acad. Sci.*, 74, 5463 (1977), etc.). The nucleotide sequence of the wild type AK gene encoded by p399AKY is shown in SEQ ID NO: 1 in Sequence Listing. The nucleotide sequence of the mutant AK gene encoded by p399AK9 is shown in SEQ ID NO: 2 in Sequence Listing. The mutant AK gene has mutation of only one base such that 1051th G is changed to A, as compared with the wild type AK. It is known for the AK gene that two subunits of α and β are encoded on an identical DNA strand in an identical reading frame (see Kalinowski, J. et al., *Molecular Microbiology* (1991) 5(5), 1197–1204). Judging from homology, it is also assumed for the genes of the present invention that two subunits of α and β are encoded on an identical DNA strand in an identical reading frame.

An amino acid sequence of the α-subunit of the wild type AK protein deduced from the nucleotide sequence of DNA is shown in SEQ ID NO: 3 in Sequence Listing. An amino acid sequence of the β-subunit is shown in SEQ ID NO: 5 in Sequence Listing. As those simultaneously showing the DNA sequence and the amino acid sequence, the α-subunit is shown in SEQ ID NO: 7 in Sequence Listing, and the β-subunit is shown in SEQ ID NO: 9 in Sequence Listing. Nucleotide sequences corresponding to open reading frame portions of each of the α- and β-subunits are shown in SEQ ID NOS: 11 and 13 in Sequence Listing, respectively.

Similarly, an amino acid sequence of the α-subunit of the mutant AK protein deduced from the nucleotide sequence of DNA is shown in SEQ ID NO: 4 in Sequence Listing. An amino acid sequence of the β-subunit is shown in SEQ ID NO: 6 in Sequence Listing. As those simultaneously showing the DNA sequence and the amino acid sequence, the α-subunit is shown in SEQ ID NO: 8 in Sequence Listing.

and the β-subunit is shown in SEQ ID NO: 10 in Sequence Listing. Nucleotide sequences corresponding to open reading frame portions of each of the α- and β-subunits are shown in SEQ ID NOS: 12 and 14 in Sequence Listing, respectively.

In each of the subunits, GTG is used as a start codon, and a corresponding amino acid is depicted as methionine. However, it is intended to represent methionine, valine, or formylmethionine. The mutation point of the mutant AK Gene implies that the mutant AK protein undergoes amino acid substitution such that 279th alanine is changed to threonine in the α-subunit, and 30th alanine is changed to threonine in the β-subunit.

Example 3

Effect on L-Lysine Productivity by Introduction of Mutant AK and Wild Type AK Plasmids into *Corynebacterium glutamicum* Wild Type Strain Strains were prepared by introducing the wild type AK plasmid p399AKYB and the mutant AK plasmid p399AK9B respectively into AJ12036 strain (FERM P-7559) as a wild type strain of *Corynebacterium glutamicum* (*Brevibacterium lactofermentum*). The genes were introduced into Corynebacterium by means of an electric pulse method. The aspartokinase activity was measured for *Corynebacterium glutamicum* (*Brevibacterium lactofermentum*) AJ12036 strain as a host, AJ12690 strain harboring the wild type AK plasmid, and AJ12691 (FERM P12918) strain harboring the mutant AK plasmid. The activity was measured in accordance with an ordinary method (see Miyajima, R. et al., *The Journal of Biochemistry* (1968) 63(2), 139–148). As shown in Table 1, it was confirmed that the introduction of the AK plasmid increased the specific activity of AK about 10–15 times, and that the synergistic inhibition by L-lysine and L-threonine was desensitized only in the strain introduced with the mutant AK plasmid. Table 1 shows specific activities of aspartokinases of cell-disrupted solutions prepared from wild type AJ12036 strain of *Corynebacterium glutamicum* (*Brevibacterium lactofermentum*), AJ12690 strain additionally harboring the wild type AK plasmid, and AJ12691 strain additionally harboring the mutant AK plasmid, and degrees of synergistic inhibition thereof by L-lysine and L-threonine. L-Lysine and L-threonine as inhibitors were added to give a final concentration of 1 mM, respectively.

TABLE 1

| Bacterial strain | AK specific activity (mU/mg protein) | |
|---|---|---|
| | No addition | +1 mM L-Lys, +1 mM L-Thr |
| AJ12036 | 19.0 | 2.6 |
| AJ12690 | 235.3 | 34.5 |
| AJ12691 | 210.5 | 145.3 |

The lysine productivity was evaluated by cultivation for the wild type strain AJ12036, the wild type AK plasmid-harboring strain AJ12690, and the mutant AK plasmid-harboring strain AJ12691 (FERM P-12918). The evaluation by cultivation was performed by inoculating the strains to a production medium (containing glucose 100 g, $(NH_4)_2SO_4$ 55 g, $KH_2PO_4$ 1 g, $MgSO_4 \cdot 7H_2O$ 1 g, soybean protein acid hydrolysate "Mamenou" (product of Ajinomoto Co., Ltd., trade name) 50 ml, $FeSO_4 \cdot 7H_2O$ 10 mg, $MnSO_4 \cdot 4H_2O$ 10 mg, nicotinic acid amide 5 mg, and $CaCO_3$ 50 g in 1 l of pure water, pH 8.0), and cultivating them with reciprocatory shaking at 31.5° C. for 72 hours. Amounts of produced lysine in culture liquids after the cultivation were as shown in Table 2. It is understood that the L-lysine productivity is remarkably improved in the strain introduced with the mutant AK plasmid. The plasmid-holding ratio upon completion of the cultivation was measured by using an index of chloramphenicol resistance as a drug resistance marker of the plasmid. It was about 100%, exhibiting extremely high stability of the plasmid (Table 2). Table 2 shows results of measurement of the L-lysine productivity by fermentation and the plasmid-holding ratio upon completion of the cultivation for wild type AJ12036 strain of *Corynebacterium glutamicum* (*Brevibacterium lactofermentum*), AJ12690 strain additionally harboring the wild type AK plasmid, and AJ12691 strain additionally harboring the mutant AK plasmid.

TABLE 2

| Bacterial strain | Amount of accumulated Lys (g/l) | Plasmid-holding ratio (%) |
|---|---|---|
| AJ12036 | 0 | — |
| AJ12690 | 2 | 100 |
| AJ12691 | 25 | 98 |

—: no available data

Example 4

Analysis of Enzymes of Wild Type AK and Mutant AK of *Corynebacterium glutamicum*

For measurement and evaluation of the enzyme activity of AK, an AK-completely deficient strain of *Escherichia coli* Gif106M1 was used as a host (Boy, E. and Patte, J. C., *J. Bacteriol.* 112, 84–92 (1972), Theze, J. et al., *J. Bacteriol.* 117, 133–143 (1974)), otherwise AK of a host and AK from a plasmid might exist in a mixed manner, resulting in impossibility to perform correct measurement, because no AK-deficient strain was present in bacteria belonging to the genus Corynebacterium. It is known that most of genes of bacteria belonging to the genus Corynebacterium are expressed in *Escherichia coli*. In addition, the AK gene was ligated at a position downstream from lac promoter on pHSG399. Thus it was postulated that the gene could be expressed in *Escherichia coli*.

At first, Gif106M1 was transformed with p399AKY and p399AK9 prepared in Example 1 to confirm growth complementation in a minimum medium M9 shown below. Thus it was confirmed that AK from the bacteria belonging to the genus Corynebacterium was expressed and operated in cells of *Escherichia coli*.

Minimum medium M9

A: 20×M9
  $Na_2HPO_4 \cdot 12H_2O$ 303 (g/L)
  $KH_2PO_4$ 60
  NaCl 10
  $NH_4Cl$ 20

B: 1M $MgSO_4$

C: 50% Glucose

D: 1 g/L Thiamine

A, B, C, and D were sterilized separately, and mixed in a ratio of A:B:C:D=5:0.1:1:0.1:95.

Subsequently, cell-free extracts were prepared from bacterial cells, and the enzyme activity of AK was measured.

Figure 2A:
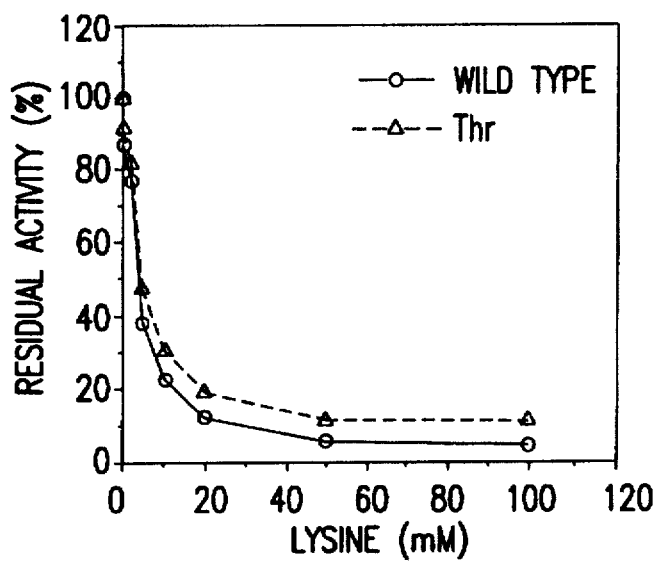
FIG. 2 shows results of investigation on inhibition by lysine, threonine, and lysine+threonine of wild type and mutant (Thr) AK's. The activity obtained without addition of lysine and threonine was regarded as 100% to indicate the activity with addition thereof as activity-holding ratios (desensitization degrees of inhibition).
Figure 2B:
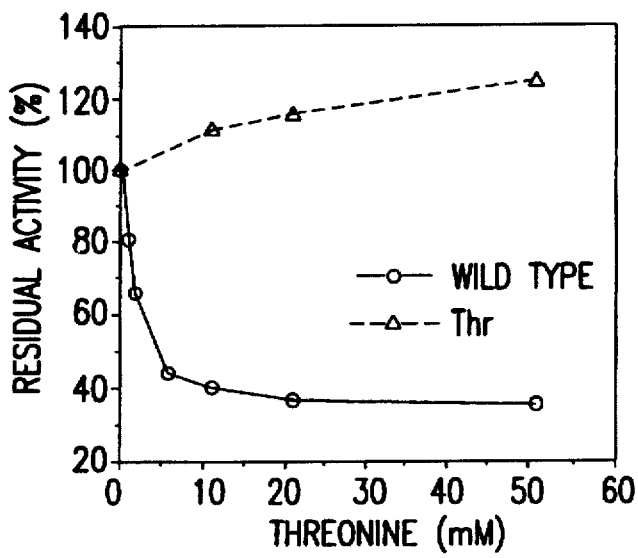
Figure 2C:
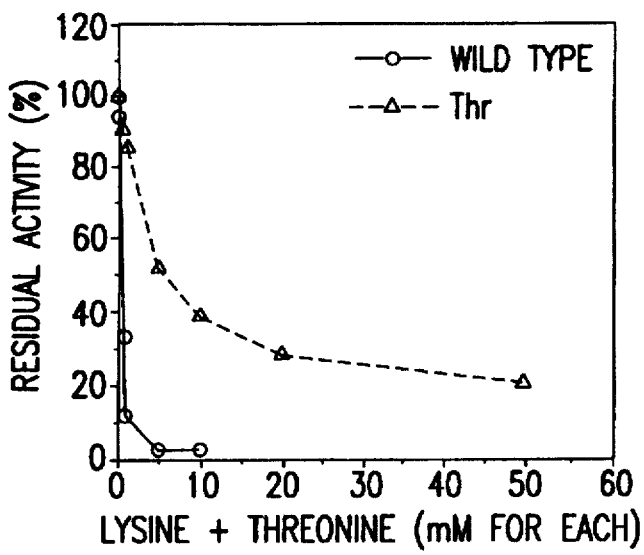

Upon measurement of the enzyme activity of AK, various concentrations of lysine and threonine were added to enzyme reaction solutions to investigate the degree of inhibition (FIG. 2). As a result, it was found that the mutant AK exhibited little improvement in inhibition by lysine alone as compared with the wild type, however, inhibition by threonine was desensitized by 100% even with activation a little, and that the desensitization of inhibition by threonine resulted in mitigation of concerted inhibition by lysine+threonine. (Ki value: 0.4 mM→5.0 mM).

Example 5

Preparation of Inhibition-Desensitized Type AK Gene of *Corynebacterium glutamicum*

It was revealed from Example 4 that the mutant AK was insufficient in desensitization of inhibition by lysine alone. Thus it was intended to improve this property by introducing mutation.

Site-directed mutagenesis was used as a method for preparing inhibition-desensitized type AK genes. It was intended to substitute the mutation point specified in Example 2 ($^{279}$Ala→Thr) with other amino acid residues. The site-directed mutagenesis method for causing objective mutation at an objective site includes, for example, a method using PCR (Higuchi, R., 61, in PCR Technology (Erlich, H. A. Eds., Stockton press (1989)), and a method using phage (Kramer, W. and Frits, H. J., *Meth. in Enzymol.*, 154 350 (1987); Kunkel, T. A. et al., *Meth. in Enzymol.*, 154 367 (1987)).

Types of amino acid residues to be introduced by mutation were as follows. Twenty kinds of amino acids were classified according to several properties such as polarity and molecular structure, and 8 kinds of representatives (Arg, Asp, Cys, Phe, Pro, Ser, Tyr, Val) were selected. Amino acid mutation and nucleotide substitution at the mutation point of each of them are shown in Table 3.

TABLE 3

| Name of mutation | Mutation point and amino acid change | Name of plasmid (name after introduction of Coryne.-ori) |
|---|---|---|
| Wild type | | p399AKY (P399AKYB) |
| Thr | $^{279}$Ala GCT → Thr A*CT | p399AK9 (p399AK9B) |
| Arg | $^{279}$Ala GCT → Arg C*G*T | p399AKAR (p399AKARB) |
| Asp | $^{279}$Ala GCT → Asp GA*T | p399AKAD |
| Cys | $^{279}$Ala GCT → Cys T*G*T | p399AKAC (p399AKACB) |
| Phe | $^{279}$Ala GCT → Phe T*T*T | p399AKAF (p399AKAFB) |
| Pro (p399AKAPB) | $^{279}$Ala GCT → Pro C*CT | p399AKAP |
| Ser (p399AKASB) | $^{279}$Ala GCT → Ser T*CT | p399AKAS |
| Tyr | $^{279}$Ala GCT → Tyr T*A*T | p399AKAY (p399AKAYB) |
| Val (p399AKAVB) | $^{279}$Ala GCT → Val GT*T | p399AKAV |

A method for introducing mutation was as follows. Eight species of synthetic DNA of 23 mer were designed, in which the codon of the 279th Ala residue for introducing mutation was substituted with the codons of the objective amino acid residues. Synthetic DNA for introducing Arg was 5'-GCCAGGCGAG CGT GCCAAGGTTT-3' (SEQ ID NO: 17), synthetic DNA for introducing Asp was 5'-GCCAGGCGAG GAT GCCAAGGTTT-3' (SEQ ID NO: 18), synthetic DNA for introducing Cys was 5'-GCCAGGCGAG TGT GCCAAGGTTT-3' (SEQ ID NO: 19), synthetic DNA for introducing Phe was 5'-GCCAGGCGAG TTT GCCAAGGTTT-3' (SEQ ID NO: 20), synthetic DNA for introducing Pro was 5'-GCCAGGCGAG CCT GCCAAGGTTT-3' (SEQ ID NO: 21), synthetic DNA for introducing Ser was 5'-GCCAGGCGAG TCT GCCAAGGTTT-3' (SEQ ID NO: 22), synthetic DNA for introducing Tyr was 5'-GCCAGGCGAG TAT GCCAAGGTTT-3' (SEQ ID NO: 23), and synthetic DNA for introducing Val was 5'-GCCAGGCGAG GTT GCCAAGGTTT-3' (SEQ ID NO: 24). Sixteen species of 23 mer single strand DNA's were synthesized together with complementary sequences thereof. For example, when the Arg residue was introduced, the single strand DNA having the sequence of 5'-GCCAGGCGAG CGT GCCAAGGTTT-3'(SEQ ID NO:17), the single strand DNA complementary thereto, the single strand DNA having the sequence of SEQ ID NO: 15, and the single strand DNA having the sequence of SEQ ID NO: 16 were used as primers to conduct the PCR method by using pB99AKY as a template. In order to exclude introduction of non-specific mutation, about 280 base pairs containing the mutation point were excised from prepared DNA by using restriction enzymes (NaeI-AvaII) to make substitution with a corresponding portion of p399AKY. The nucleotide sequence was confirmed for the substituted region.

Example 6

Analysis of 8 Kinds of Enzymes of Mutant AK Genes

Figure 3:
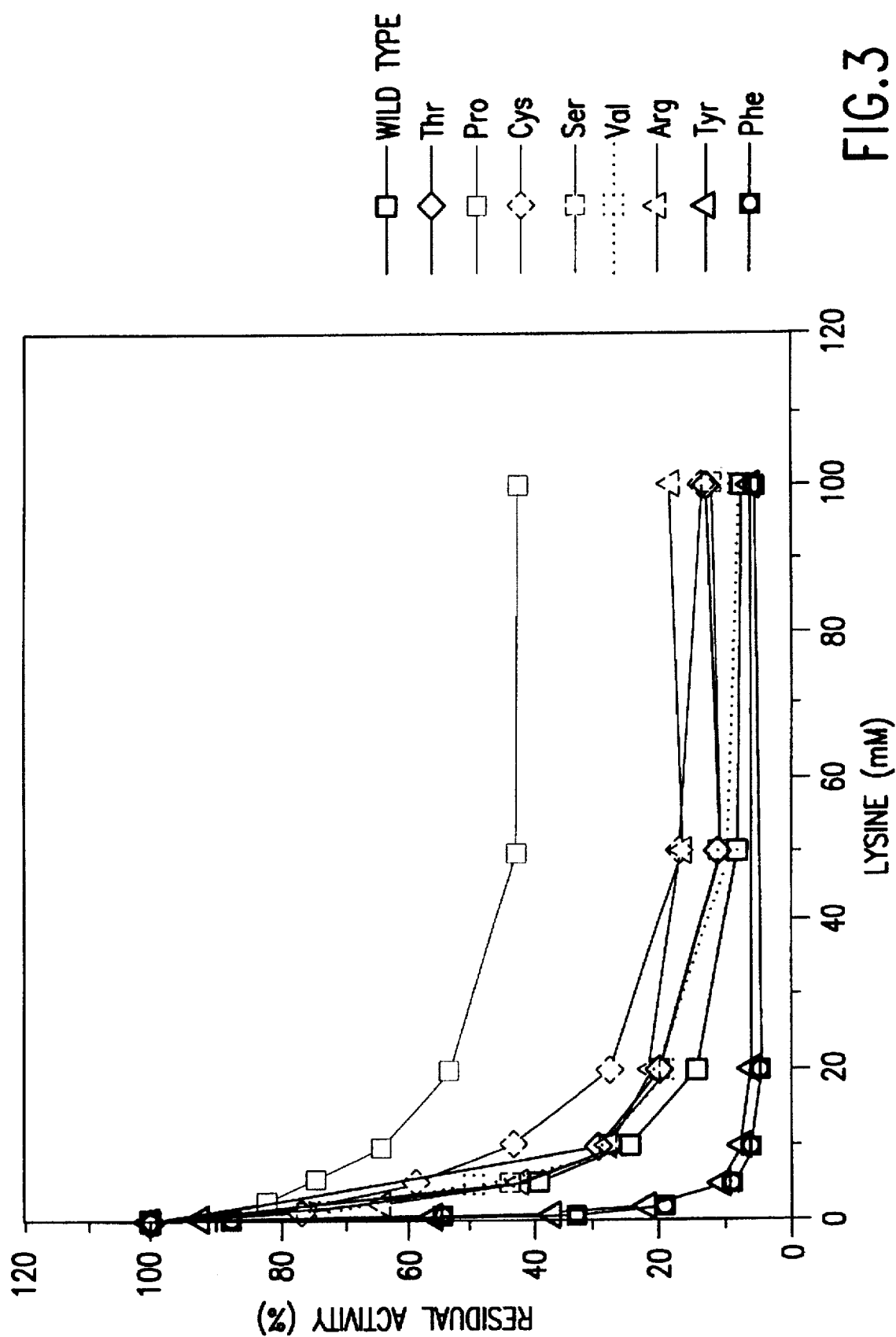
FIG. 3 shows results of investigation on desensitization degrees of inhibition by lysine for 8 kinds of AK's of the wild type and mutants.
Figure 4:
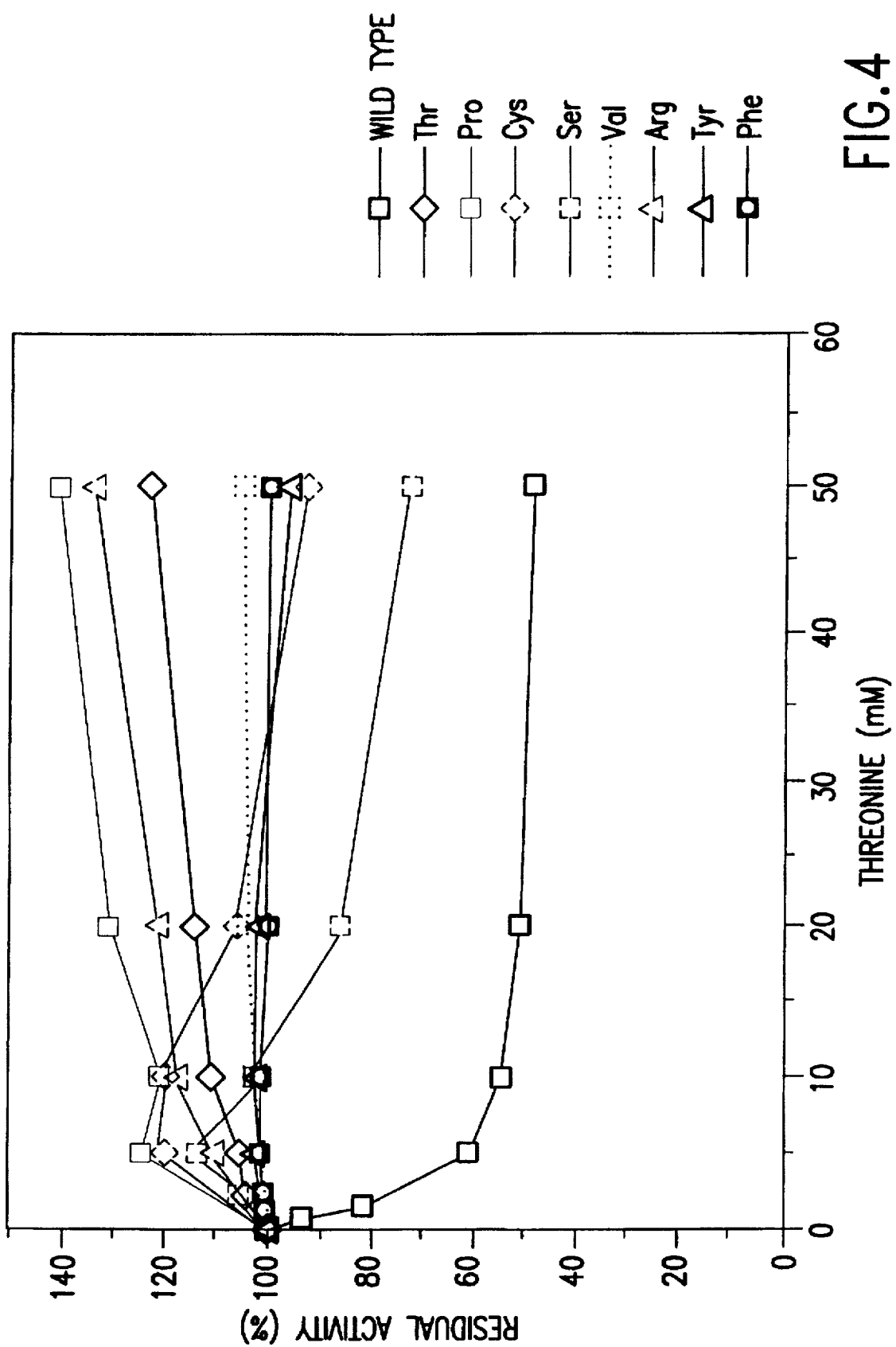
FIG. 4 shows results of investigation on desensitization degrees of inhibition by threonine for 8 kinds of AK's of the wild type and mutants.
Figure 5:
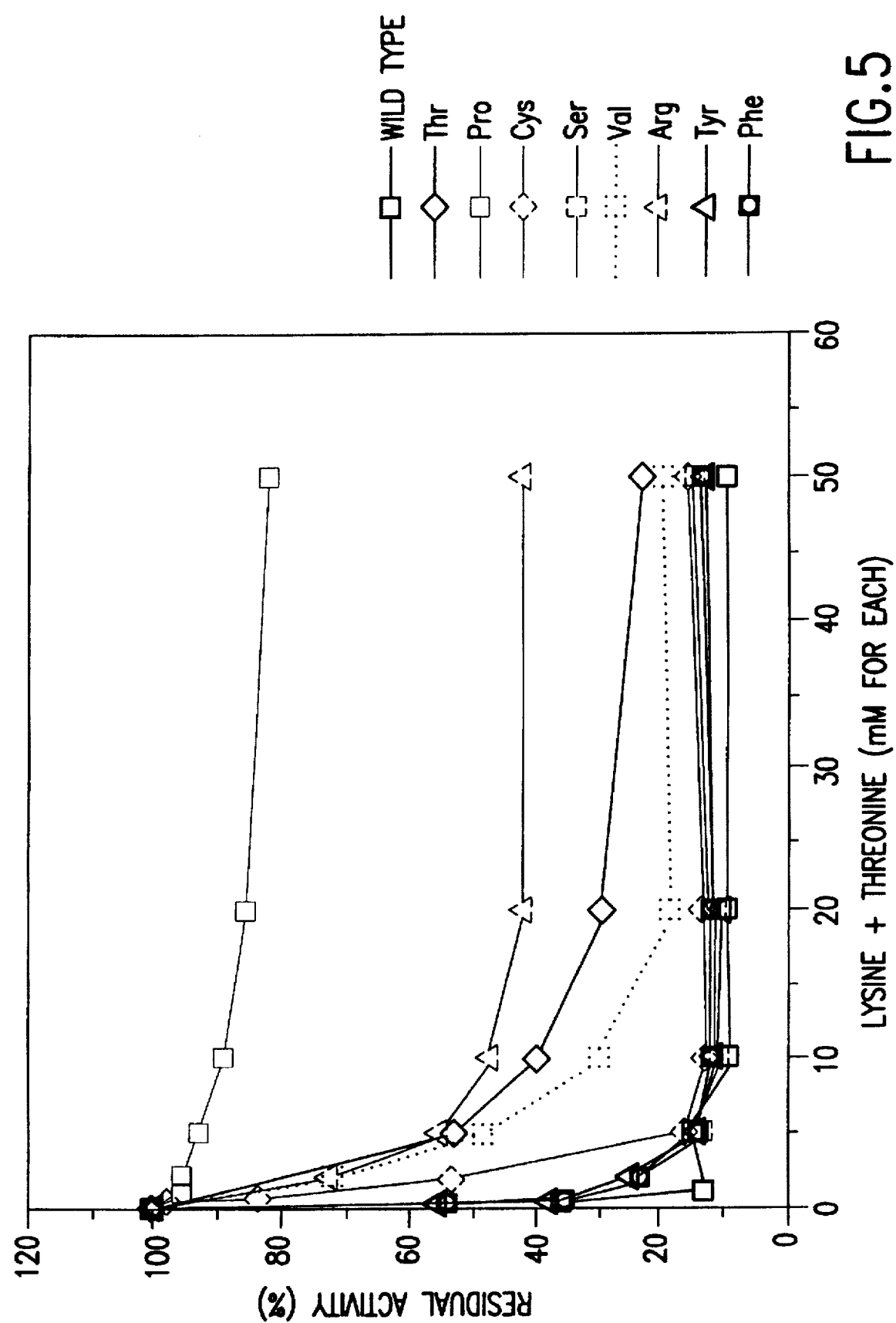
FIG. 5 shows results of investigation on desensitization degrees of concerted inhibition by lysine+threonine for 8 kinds of AK's of the wild type and mutants.

Gif106M1 was transformed with 8 kinds of the plasmids containing each of the mutant AK genes obtained in Example 5 in accordance with a method similar to that in Example 4. Cell-free extracts were prepared, and enzymes were analyzed. The degree of desensitization of inhibition, and the specific activity upon addition of lysine 5 mM, threonine 5 mM, or lysine 5 mM+threonine 5 mM are shown in Table 4. The degree of desensitization of inhibition upon addition of each concentration of lysine and/or threonine is graphically shown in FIGS. 3, 4 and 5.

TABLE 4

| | Specific activity (mU/mg protein) | 5 mM Lys (%) | 5 mM Thr (%) | 5 mM Lys + Thr (%) |
|---|---|---|---|---|
| Wild type | 15.3 | 42.3 | 62.3 | 9.2 |
| Thr | 12.9 | 47.0 | 103.5 | 50.4 |
| Pro | 2.8 | 76.9 | 126.9 | 103.8 |
| Cys | 15.4 | 56.3 | 108.1 | 17.0 |
| Ser | 8.2 | 52.6 | 131.6 | 18.4 |
| Val | 21.8 | 51.1 | 98.3 | 52.3 |
| Arg | 7.6 | 40.6 | 107.2 | 47.8 |
| Tyr | 14.4 | 14.4 | 103.6 | 19.4 |
| Phe | 18.7 | 12.1 | 103.0 | 18.2 |
| Asp | 1.5 | — | — | — |

AK was inactivated in the case of change to acidic amino acid such as Asp. However, the inhibition by threonine was desensitized in the case of change to any other amino acid. The mutation could be generally classified into 4 groups for other properties. Mutation similar to the mutant (Thr) in Example 2 includes the Val residue-introduced mutant strain, and the Arg residue-introduced mutant strain. As for the Cys residue-introduced mutant strain and the Ser residue-introduced mutant strain, the inhibition by lysine alone was equivalent to that in the wild type, however, the inhibition was consequently enhanced in the case of the concerted inhibition. The concerted inhibition has been enhanced probably because the behavior to threonine has a characteristic property to give a crest-shaped graph such that activation occurs at low concentrations but inhibition occurs at high concentrations. The inhibition by lysine alone Was enhanced in the Phe residue-introduced mutant strain and the Tyr residue-introduced mutant strain concerning aromatic amino acids, as compared with the wild type. The Pro residue-introduced mutant strain had a low specific activity (about 1/5 of that of the wild type) probably because Pro might greatly affect the stereochemical structure. However, the inhibition by lysine alone was mitigated, and the degree of activation by threonine became large (not less than 120%). Thus the concerted inhibition was also desensitized.

Figure 6:
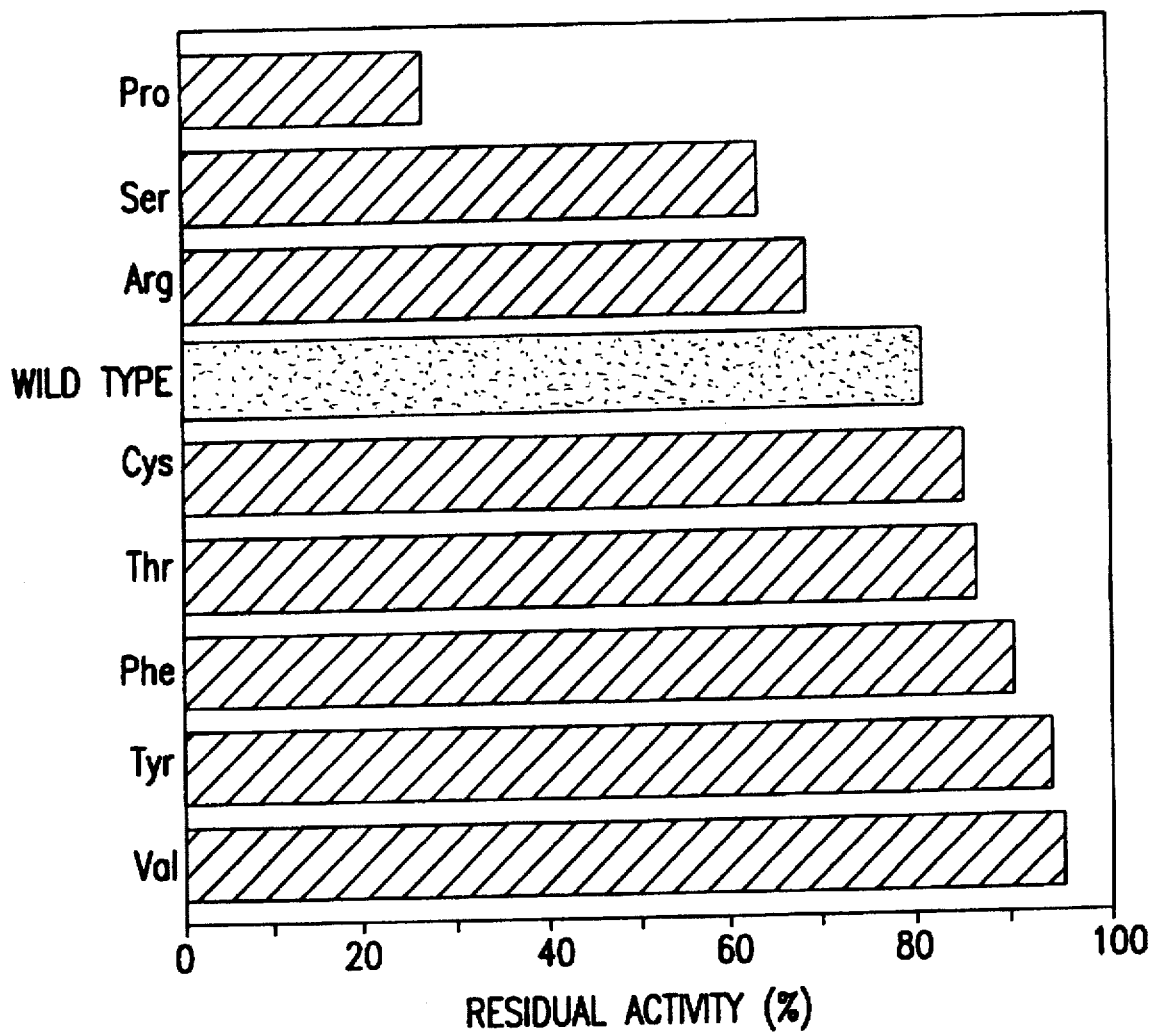
FIG. 6 shows results of investigation on thermal stability for 8 kinds of AK's of the wild type and mutants. The activity-holding ratio after a treatment at 55° C. for 90 minutes is indicated by %.

Thermal stability was investigated as an index of stability of the enzyme structure constructed by the introduction of mutation. The treatment condition was set at 55° C. for 1.5 hour in which the activity of the wild type AK was about 80%. The Cys residue-introduced mutant strain, the Thr residue-introduced mutant strain, the Phe residue-introduced mutant strain, the Tyr residue-introduced mutant strain, and the Val residue-introduced mutant strain had higher stability than that of the wild type, among which the Val residue-introduced mutant strain had the highest stability (FIG. 6).

Example 7

Effect on L-Lysine Productivity by Introduction of Plasmids Containing 8 Kinds of Mutant AK Genes and Wild Type AK Gene into *Corynebacterium glutamicum* Wild type strain Strains were prepared by introducing 8 kinds of the plasmids shown in Table 3 into AJ12036 strain (FERM P-7559) as a wild type strain of *Corynebacterium glutamicum* (*Brevibacterium lactofermentum*) in the same manner as Example 3. The AK activity was measured for each of the strains. As shown in Table 5, the AK specific activities of the strains introduced with each of the plasmids were increased about 20–80 times as compared with the AK specific activity of the host. The desensitization degree of inhibition by lysine and/or threonine was similar to those in Example 6. The Pro residue-introduced mutant AK had the highest degree of desensitization of inhibition, in which the degree of desensitization of inhibition was greater than that of the Thr reside-introduced mutant AK, with respect to any of the inhibition by lysine alone, the inhibition by threonine alone, and the concerted inhibition by the both.

TABLE 5

|  | Specific activity (mU/mg protein) | 5 mM Lys (%) | 5 mM Thr (%) | 2 mM Lys + Thr (%) |
| --- | --- | --- | --- | --- |
| AJ12036 | 5.6 | 52.0 | 82.0 | 7.0 |
| Wild type | 316.4 | 52.7 | 86.8 | 6.2 |
| Thr | 374.4 | 58.7 | 109.1 | 78.3 |
| Arg | 197.4 | 41.4 | 106.8 | 58.6 |
| Cys | 267.0 | 66.5 | 135.7 | 60.6 |
| Phe | 447.7 | 14.6 | 105.0 | 32.4 |

TABLE 5-continued

|  | Specific activity (mU/mg protein) | 5 mM Lys (%) | 5 mM Thr (%) | 2 mM Lys + Thr (%) |
| --- | --- | --- | --- | --- |
| Pro | 125.0 | 77.5 | 123.2 | 85.2 |
| Ser | 406.8 | 55.0 | 114.4 | 37.0 |
| Tyr | 425.6 | 16.1 | 104.8 | 32.2 |
| Val | 448.9 | 60.5 | 103.5 | 75.5 |

The lysine productivity was further evaluated by cultivation for the 9 kinds of these strains by using a method similar to that in Example 3. The amount of produced lysine in each cultivation is as shown in Table 6. It is understood that the L-lysine productivity is remarkably improved by introducing the mutant AK plasmids. Especially, high accumulation of about 25 g/l was exhibited in the mutant strains other than the Cys residue-introduced mutant strain and the Set residue-introduced mutant strain. The plasmid-holding ratio upon completion of the cultivation was approximately 100%, exhibiting high stability of the plasmids.

TABLE 6

|  | Lys—HCl (g/l) | Plasmid holding ratio (%) |
| --- | --- | --- |
| Wild type | 0.00 | 100 |
| Thr | 24.25 | 100 |
| Arg | 24.56 | 100 |
| Cys | 13.41 | 100 |
| Phe | 25.14 | 100 |
| Pro | 25.11 | 100 |
| Ser | 5.72 | 100 |
| Tyr | 25.12 | 100 |
| Val | 25.02 | 100 |

Industrial Applicability

In the AK gene of *Brevibacterium lactofermentum*, Ala located at the position 279 in accordance with the amino acid numbers in SEQ ID NO: 3 or at the position 30 in accordance with the amino acid numbers in SEQ ID NO:5 was changed to amino acids other than acidic amino acids. Thus AK was obtained in which inhibition by threonine was completely desensitized, and consequently concerted inhibition by lysine+threonine was desensitized. Especially, AK was obtained, in which inhibition by lysine alone was partially desensitized, by changing the amino acid residue at the aforementioned position to Pro. AK having improved thermal stability was obtained by changing the aforementioned site to Val, Tyr, or Phe. The productivity of L-lysine could be remarkably increased by increasing the activity of such mutant AK in cells of coryneform bacteria.

What is claimed is:

1. A recombinant DNA fragment coding for an aspartokinase α-subunit protein originating from a bacterium belonging to the genus Corynebacterium, in which synergistic feedback inhibition by L-lysine and L-threonine is substantially desensitized, said protein having an amino acid sequence defined by SEQ ID NO: 4, or a sequence in which the 279th residue in said amino acid sequence is changed to an amino acid other than Ala and other than acidic amino acids.

2. A recombinant DNA fragment coding for an aspartokinase β-subunit protein originating from a bacterium belonging to the genus Corynebacterium, in which synergistic feedback inhibition by L-lysine and L-threonine is substantially desensitized, said protein having an amino acid sequence defined by SEQ ID NO: 6, or a sequence in which a 30th residue in said amino acid sequence is changed to an amino acid residue other than Ala and other than acidic amino acids.

3. The DNA fragment according to claim 1, having a nucleotide sequence defined by SEQ ID NO: 12.

4. The DNA fragment according to claim 2, having a nucleotide sequence defined by SEQ ID NO: 14.

5. Recombinant DNA containing the DNA fragment as defined in claim 1 and being replicable in microorganisms belonging to the genus Corynebacterium.

6. A transformant obtained by introducing the recombinant DNA as defined in claim 5 into a microorganism belonging to the genus Corynebacterium, wherein the specific activity of aspartokinase is increased 2–20 times as compared with a parent strain, and synergistic feedback inhibition by L-lysine and L-threonine or feedback inhibition by L-lysine alone exerted on the activity of aspartokinase is substantially desensitized.

7. A method of producing L-lysine, comprising the steps of:

cultivating the transformant as defined in claim 6 in an appropriate medium; and separating produced L-lysine.

8. An aspartokinase α-subunit protein originating from a bacterium belonging to the genus Corynebacterium, in which synergistic feedback inhibition by L-lysine and L-threonine is substantially desensitized, said protein having an amino acid sequence defined by SEQ ID NO: 4, or a sequence in which a 270th residue in said amino acid sequence is changed to an amino acid residue other than Ala and other than acidic amino acids.

9. An aspartokinase β-subunit protein originating from a bacterium belonging to the genus Corynebacterium, in which synergistic feedback inhibition by L-lysine and L-threonine is substantially desensitized, said protein having an amino acid sequence defined by SEQ ID NO: 6, or a sequence in which a 30th residue in said amino acid sequence is changed to an amino acid residue other than Ala and other than acidic amino acids.

10. Recombinant DNA containing the DNA fragment as defined in claim 2 and being replicable in microorganisms belonging to the genus Corynebacterium.

11. Recombinant DNA containing the DNA fragment as defined in claim 3 and being replicable in microorganisms belonging to the genus Corynebacterium.

12. Recombinant DNA containing the DNA fragment as defined in claim 4 and being replicable in microorganisms belonging to the genus Corynebacterium.

* * * * *